US007063853B1

(12) United States Patent
Brunham

(10) Patent No.: US 7,063,853 B1
(45) Date of Patent: Jun. 20, 2006

(54) DNA IMMUNIZATION AGAINST CHLAMYDIA INFECTION

(75) Inventor: Robert C. Brunham, Vancouver (CA)

(73) Assignee: University of Manitoba, Winnipeg (CA)

( * ) Notice: Subject to any disclaimer, the term of this patent is extended or adjusted under 35 U.S.C. 154(b) by 0 days.

(21) Appl. No.: 09/647,946

(22) PCT Filed: Apr. 7, 1999

(86) PCT No.: PCT/CA99/00292

§ 371 (c)(1),
(2), (4) Date: Dec. 6, 2000

(87) PCT Pub. No.: WO99/51745

PCT Pub. Date: Oct. 14, 1999

(51) Int. Cl.
*A61K 39/118* (2006.01)
*A61K 39/00* (2006.01)
*C07H 1/00* (2006.01)
*C07H 19/00* (2006.01)
*C07H 21/02* (2006.01)

(52) U.S. Cl. .................. 424/263.1; 424/88; 424/92; 424/185.1; 530/300; 530/350; 536/22.1; 536/23.1; 536/23.7

(58) Field of Classification Search .................. 424/88, 424/92, 185.1, 263.1; 530/300, 350; 536/22.1, 536/23.1, 23.7
See application file for complete search history.

(56) References Cited

U.S. PATENT DOCUMENTS

| 5,589,466 | A | 12/1996 | Felgner et al. | |
|---|---|---|---|---|
| 6,235,290 | B1 * | 5/2001 | Brunham | 424/263.1 |
| 6,344,202 | B1 * | 2/2002 | Brunham | 424/263.1 |

FOREIGN PATENT DOCUMENTS

| EP | 0 192 033 A2 | 8/1986 |
|---|---|---|
| WO | WO 98/02546 | 1/1998 |

OTHER PUBLICATIONS

Baxby, D., et al, "Potential use of non-replicating vectors as recombinant vaccines" Vaccine, 1992, vol. 10, No. 1, pp. 8-9.*
Dascher, C., et al, "Expression and translocation of the chlamydial major outer membrane protein in *Escherichia coli*.", Microbial Pathogenesis, 1993, vol. 15, pp. 455-467.*
Douglas, A.L., et al, "Mutagenesis of the P2 promoter of the major outer membrane protein gene of *Chlamydia trachomatis*", Journal of Bacteriology, 1996, vol. 178, No. 19, pp. 5573-5578.*
Kaul, R., et al "Expression of the *Chlamydia trachomatis* major outer membrane protein-encoding gene is *Escherichia coli*: role of the 3' end in mRNA stability." Gene, 1990, vol. 87, No. 1, pp. 97-103.*
Anderson, R., et al, "Immune response in mice following immunization with DNA encoding fragment C of tetanus toxin." Infection and Immunity, 1996, vol. 64, No. 8, pp. 3168-3173.*
Donnelly et al, Ann. N.Y. Acad. Sci. 772 (1995) pp. 40-46.
D. M. Pardoll and A. M. Beckerieg, Immunity 3, 165-169 (1995).
W.M. McDonnell and F. K. Askari, N. Engl. J. Med. 334, 42-45 (1996).
J. B. Ulmer et al., Science 259, 1745-1749 (1993).
B. Wang et al., Proc. Natl. Acad.. Sci. USA 90,4156 (1993).
G. J. M. Cox, T.J. Zamb, L.A. Babiuk, J. Virol. 67, 5664-5667(1993).
E. Raz et al., Proc. Natl.Acad. Sci. USA, 91,9519-9523(1994).
Z. Q. Xiang et al., Virology 199, 132-140 (1994).
J.J.Donnelly et al., J. Infect. Dis. 713, 314-320 (1996).
D. L. Montgomery et al., DNA. Cell. Biol. 12, 777-783 (1993).
J.J. Donnelly et al., Nature Medicine 1, 583-587 (1995).
G. H. Rhodes et al., Dev. Biol.Stand. 82, 229 (1994).
H. L. Davis, M. L Michel, R. G. Whalen, Human Molecular Genetics 2, 1847-1851 (1993).
J. B. Ulmer et al., Vaccine 12, 1541-1544 (1994).
E. F. Fynan et al, Proc. Natl. Acad. Sci. USA 90, 11478-11482 (1993).
E. Manickan, R. J. D. Rouse, Z. Yu, J. Immunol. 155, 259-265 (1995).
M. Sedegah, R. Hedstorm, P. Hobart, S. L. Hoffman, Proc. Natl. Acad. Sci. USA 91, 9866-9870 (1994).
M.A. Barry, W.C. Lai, S.A. Johnston, Nature 377, 632-635 (1995).
D. Xu and F. Y. Liew, Vaccine 12, 1534-1536 (1994).
D. B. Lowrie, R.E. Tascon, M. J. Colston, Vaccine 12, 1537-1540 (1994).
J. W. Moulder, Microbiol. Rev. 55, 143-190 (1991).
J. Schachter, Curr. Top. Microbiol. Immunol, 138, 109 (1988).
S. D. Hillis and J. N. Wasserheit,N. Engl. J. Med. 334, 1399-1401 (1966).
R. C. Brunham and R. W. Peeling, Infectious Agents and Disease 3, 218-233 (1994).

(Continued)

*Primary Examiner*—Rodney P Swartz
(74) *Attorney, Agent, or Firm*—Sim & McBurney

(57) ABSTRACT

Nucleic acid, including DNA, for immunization to generate a protective immune response in a host, including humans, to a major outer membrane protein of a strain of *Chlamydia*, preferably contains a nucleotide sequence encoding a fragment that generates antibodies that specifically react with MOMP and a promoter sequence operatively coupled to the first nucleotide sequence for expression of the MOMP fragment in the host. The non-replicating vector may be formulated with a pharmaceutically-acceptable carrier for in vivo administration to the host.

25 Claims, 15 Drawing Sheets

OTHER PUBLICATIONS

T. Grayston and S-P. Wang, Sex Trans. Dis. 5, 73-77 (1978).
J.T. Grayston and S.-P Wang, J. Infect.Dis. 132, 87-105 (1975).
H. R. Taylor, J. Whittum-Hudson, J. Schachter, Invest. Ophthalmol. Vis. Sci. 29, 1847-1853 (1988).
B.E. Batteiger, R. G. Rank, P.M. Bavoil, J. Gen. Microbiol, 139, 2965-2972 (1993).
M. Campos et al., Invest. Ophthalmol. Vis. Sci. 36, 1477-1491 (1995).
H. Su, M. Parne, H. D. Caldwell, Vaccine 13, 1023-1032 (1995).
T. -W. Tan, A.J. Herring, I. E. Anderson, Infect. Immun. 58, 3101-3108 (1990).
M. Tuffrey, F. Alexander, W. Conlan, J. Gen. Microbiol. 138, 1707-1715 (1992).
Y. - X. Zhang, J. G. Fox, Y. Ho, Mol. Biol. Evol. 10, 1327-1342 (1993).
R. P. Morrison, K. Feilzer, D. B. Tumas, Infect. Immun. 63, 4661-4668 (1995).
H. Su and H. D. Caldwell, Infect. Immun. 63, 3302-3308 (1995).
J. U. Igietseme et al., Reg.Immunol. 5, 317-324 (1993).
J. U. Igietseme and R. G. Rank, Infect. Immun. 59, 1346-1351 (1991).
D. M. Williams, J. Schachter, J.J. Coalson, J. Infect. Dis. 149, 630-639 (1984).
G. Tipples and G. McClarty, J. Biol. Chem. 270, 7908-7914 (1995).
X. Yang, K. T. HayGlass, R. C. Brunham, J. Immunol., 156, 4338-4344 (1996).
H. Su and H. D. Caldwell, Infect. Immun. 63, 946-953 (1995).
A. S. McWilliam, D. Nelson, J.A. Thomas, J. Exp. Med. 179, 1331-1336 (1994).
M. R. Neutra, E. Pringault, J.-P. Kraehenbuhl, Annu. Rev. Immunol. 14, 275-300 (1996).
J.M. Austyn, J. Exp. Med. 183, 1287-1292 (1996).
R. Brunham et al., J. Clin. Invest. (94)1, 458-463 (1994).
R. C. Brunham et al., J. Infect. Dis. 173 950-956 (1996).
Tang et al., Nature 1992, 356: 152-154.
Morrison RP, Manning DS, Caldwell HD. Immunology of Chlamydia trachomatis infections. Immunoprotective and immunopathogenetic responses. In: Quin TC. Advances in host defence mechanisms. Sexually transmitted diseases. vol. 8. New York: Raven Press, 1992: 57-84.
Xiang Z. Ertl HCJ. Manipulation of the immune response to a plasmid-encoded viral antigen by coinoculation with plasmids expressing cytokines. Immunity 1995: 2:129-35.
Holland M. J. et al., Synthetic peptides based on *Chlamydia trachomatis* antigens identify cytotoxic T lymphocyte responses in subjects from a trachoma-endemic population. Clin. Exp. Immunol Jan. 1997; 107 (1): 44-49.
Su, H. et al, Identification and characterization of T-helper cell epitopes of the major outer membrane protein of *Chlamydia trachomatis*, J. Exp.Med. Jul. 1, 1990: 172 (1): 203-212.
Su, H et al, Immunogenicity of a chimeric peptide corresponding to T helper and B cell epitopes of the *Chlamydia trachomatis* mmajor outer membrane protein, J. Exp. Med. Jul. 1, 1990; 175 (1):227-235.
Allen, J. E. et al A single peptide from the major outer membrane protein of *Chlamydia trachomatis* elicits T cell help for the production of antibodies to production of antibodies to protective determinants. J. Immunol. Jul. 15, 1991; 147 92; 674-679.
Davis et al. Vaccine 1994; 12:1503-1509.
Lopez-Macia et al., "Induction of Antibodies against *Solmonella typhi* OmpC Porin by naked DNA immunization" Annals of the New York Academy of Science, vol. 772, 1995, pp. 129-135.
Liu, M.A. et al., N.Y. Acad. Sci. 772 (1995).
Knight, S.C. et al. A peptide of *Chlamydia trachomatis* shown to be a primary T-cell epitope in vitro induces cell-mediated immunity in vivo. PMID: 1712817, UI:91302820, Immunology May 15, 1995, 85(1), pp. 8-15.
Zhang Dong-Ji. et al. Intramuscular Immunization. 1997, pp. 113-117.
Barnet LouAnn, et al., Journal of neuroimmunology 64 (1996) 163-173.
Douglas A. and Hatch P. T., Journal of Biology 1996. p. 5573-5578.
Baxby D. and Paoletti E. Vaccine vol. 10, 1992. pp. 8-9.
Chen Z. et al. Vaccine Research vol. 4, 1995, p.135-144.
Brunham C. R. et al. Transgene as vaccine for *chlamydia*. 1999; 138:S519-S522.
Robinson L. Harriet, Vaccine 1997 vol. 15 pp. 785-787.
McCluskie, J.M. et al. Molecular Medicine 5: 287-300. 1999.
Green S. et al. Liposomal Vaccine. vol. 383 : pp. 83-92.

* cited by examiner

FIG. 10A

```
                1                                         26       29
E     MKLLKSVLVFAAL-SSASSLQALPVGNPAEPSIMIDGILWEGFCGDP C D
B     ..........................................
L1    ..........................................
DA    ..........................................
L2    ..........................................
F     ..........................................
L3    ..........................................
A     ..........................................
C     .........A...V.-G....H....................
H     .........A...V.-G....H....................
MoPn  .........A.L..T-G.L................L..TM..AS.
SFPD  .........A.L..TT-G.L...............L..TM..AS.
GPIC  .........A.LS..FAG.VG...........SD.L..TI..AA.
Mn
HuPn
```

```
       23                              59              VD I
P C TTW C DAISMRMGYYGDFVFDRVLKTIDVNK EFQ-MGDKPTSTIGNATAPTT  78
        ..........................  -...A..T....V..S.    78
        ..........................  -...A....A..A..S.    78
        ..................Q.......  H-..A....TD..SA..S.   78
        ..................E.......  ...A....TA..A..S.    78
        ..................Q.......  -...A....A..A..S.    78
```

FIG.10B

|    |           |           |                  |                        | # |
|----|-----------|-----------|------------------|------------------------|---|
| E  | .......... | .......... | ..........      | E-..EALAGAS..T.-S.     | 76 |
| B  | .......... | .......... | V.........      | ...AE..TSDIAGL-SND     | 77 |
| L1 | .......... | .......... | ..........      | -I...AA..TSDIAGL-EKD   | 77 |
| DA | .......... | .......... | V.........      | ...AA..TSDIAGL-QND     | 77 |
| L2 | .......... | .......... | V.........      | ...AA..TNDAADL-QND     | 77 |
| F  | .......... | ....A..... | L.L........     | Q.E-..AA.G-DADL.TAP.   | 77 |
| L3 | .......... | .......... | L.L........     | Q.E-..PV.T.DTD.A.DI.   | 76 |
| A  | .......... | ....S..... | I.A..Y..I.V     | TIS..TA.---N.A.DFK     | 75 |
| C  | .......... | ....A..... | I.A..Y....V     | T.SG.AAT..QA..N.SNINQ  | 79 |
| H  | .......... | ....A..... | L.A.F.Y..I.V.AP | T.S-..A....---S.A.--N  | 73 |

Position 83 / 115

|    | LT---ARE | NPAYGRHMQDAEMFTNAACMALNIWDREDVF | C | TLGASSGYL |
|----|----------|----------------------------------|---|-----------|
| E  | LT---ARE | NPAYGRHMQDAEMFTNAACMALNIWDREDVF  | C | TLGASSGYL |
| B  | ..C.---  | ...............................  | . | T........ |
| L1 | ..C.---  | ...............................  | . | T........ |
| DA | ..C.---  | .............Y.................  | . | T........ |
| L2 | ..C.---  | ...............................  | . | T........ |
| F  | .SKLVE.T | ......................T........  | . | T........ |
| L3 | P.TNV..P | ....K..........................  | . | TT....... |
| A  | PVANV..P | ....K........Y..................  | . | TT....... |
| C  | P.TNV..P | ....K........Y..................  | . | TT....... |
| H  | PKTNV..P | ....K........Y..................  | . | TT....... |

FIG. 10C

```
             |                                                   |139
MoPn   -PA--S..  ..........K..........Y..............T.....
SFPD   TST--P..  ..........K..........Y..............T.....
GPIC   TVA--D.N  I...K.....WS.........FL............N.......
Mn     PEAN-G.P  I.........E..W.S.....FL..I.........N.F.....
HuPm   Y.TAVD.P  ....NK.IH..W......GFI..............N.I.....

┌─── VD II ────────────────────────────────────┐   159
       KGNSASFNLVGLFG DNENQSTVKTNS-----VPNMSLDQS VVELYTDTAFSWSVG  174
       ..............N....TK..SNGAF----........ ...............  175
       ..................KDA--------...F....... .....A.........  174
       ..................K...AE.-----..F....... .T.A...........  174
       ..............HA..SDSKL------........... ...T.A.........  175
       ...........GV.ATKPAAD.----I...VQ.N...... ...T.A.........  175
       ..............TKTQSTNFN.AKL---..TA.N.A.. ...T.A.........  177
       ..............TKTQS.GFD.ANI---..TA.N.A.. ...T.A.........  177
       ..............TKTQS.SFN.AKL--I..TA.NEA.. IN.T.A.........  177
       ..............TKTKS.DFN.AKL---..IA.NRA.. ...T.A.........  177
       .......A......RD.TA----VAADDI.V..S.A.... .....A.........  171
       ..............GVANAANAIATVAADSL.V..S.A.. .....A.........  180
       .A.A..........L.VTG---TDLQGQ---Y..VAIS.G L.....T........  169
       .AS..A........I.FSAAS.ISTDLPTQ---L..VGIT.G ..F....S.......  178
       .R...TA.......VKG--T..N-ANE----L.V..SNG. ...........S...  170
```

FIG.10D

```
              182 184                            210
       ARAALME C G C ATLGASFQYAQSKPKVEELNVL C NAAEFTINKPKGY
E      ....... . . . ..................... . ............
B      ....... . . . ..................... . ............
L1     ....... . . . ..................... . ............
DA     ....... . . . ..................... . ............
L2     ....... . . . .........I........... . ............
F      ....... . . . ..................... . ....D.S.....
L3     ....... . . . ..................... . .......S....
A      ....... . . . ..................... . .......S....
C      ....... . . . ..................... . .......S....
H      ....... . . . ..................... . .......S....
MoPn   ....... . . . ..................... . .....Q......
SFPD   ....... . . . ..................... . ............
GPIC   ..G.... . . . ....E...N..I.M...I S SPTQ.V.H..R..
Mn     ..G.... . . . ....E...N..I.M...T S SP.Q.V.H..R..
HuPn   ..G.... . . . ....E............... . .VSQ.SV.....
                                         223              233

VD III
VG --QEFPLALIAGTDA ATGTKDASIDYHEMQASLALSYRLNMFTPYIGVKWSRA  273
.. --.-K.L..D.T.. ...........................            274
.. --.-K...D.T.. ...........................             273
.. --.-K...D.T.. ...........................             273
.. --.-..D.K...G V............................           274
```

FIG. 10E

```
       SFDADTIRIRLAQPK SATAIFDTTLNPTIAGAG-DVKASA-----EGQLG DT
       287                                              316
                      ──────────VD IV──────────

E   ...............  ................................. ..  --K....D.T.......S..........  274
B   ...............  ....ET..V........T.............. ..  --A....DIT...E..............  276
L1  ...............  ....L...........-E..N..---....... ..  --A....DIT...E..............V  276
DA  ...............  ................-...TGT--........ ..  --A....NIT...E..............V  276
L2  ...............  ....TV..V.......-................ ..  --A....DIT...E..............V  276
F   .....S.........R  LV.PWV.I........C.-S.AGANT--..IS ..  --....NIK..VS..D............V  276
L3  ...............  L.E.VL.V........K.-S.V..GS---NE.A ..  --.....K.......D............  270
A   ...............  L.KPVL..........K.-T.VS..---NE.A  ..  K.TAAN..P.T..ES.D.S.T.K...IG.....LV...N.....  279
C   ...............  L.E.LV..........K.-S.VSAGT--DNE.A ..  K.ASSN..PIT..TE.D.S.T.K...VG.....LV...N.....  270
H   ...............  L.E.LV..........K.-T.V..GS---DNE.A ..  ..........S.T.N.....VGAS.....SLV....Q.....  280
MoPn ...............  LE.S.LKM..W....S.S.I.---------DTKIT ..  K.--VA...PTD..VAT............  269
```

FIG. 10F

```
SFPD  ..........  L.E..L.V..W.........TIADGTGAAATANG.A..
GPIC  T....S.....  LP...INL.W..LL.---EATTINIG---AKYA..Q
Mn    T..........  LKSE.INI.W..SLI.ST-TALPNNSGK---DV.S.V
HuPn  T....N.....  LP..VLNL.AW..SLL.---NAT.LSTT---DSFS.F
                                    335
```

```
       MQIVSLQLNKMKSRKS C GIAVGTTIVDADKYAVTVETRLIDERAAHVNAQFRF   371
       ...............  . ..................................   372
       ...............  . ..................................   371
       ...............  . ..................................   371
       ...............  . ..................................   372
       ...............  . ..................................   373
       ...............  . .............V......................  375
       ...............  . ...............I...................   374
       ...............  . ..A.................................  375
       ...............  . .LI................................   375
       ...L...........  . .LI................................   365
       ...L.A..I......A . A.LI...WSI.G.A..N.................   382
       ...L.A.II......A . V.A.LI...WSI.G.A..N.................  367
       ...L.A.II......A . V..A.L....WSL.A.A..N.....M..........  380
       ......C.I.F....A . VT.A.L....WSL.A.A..N.........SG.....  366
```

DNA IMMUNIZATION AGAINST *CHLAMYDIA* INFECTION

REFERENCE TO RELATED APPLICATIONS

This application is a national phase application under 35 U.S.C. 371 of PCT/CA99/00292 filed Apr. 7, 1999, which claims priority from U.S. patent application Ser. No. 09/055,765 filed Apr. 7, 1998 (now U.S. Pat. No. 6,344,202).

FIELD OF INVENTION

The present invention relates to immunology and, in particular, to immunization of hosts using nucleic acid to provide protection against infection by *Chlamydia*.

BACKGROUND OF THE INVENTION

DNA immunization is an approach for generating protective immunity against infectious diseases (ref. 1—throughout this application, various references are cited in parentheses to describe more fully the state of the art to which this invention pertains. Full bibliographic information for each citation is found at the end of the specification, immediately preceding the claims. The disclosure of these references are hereby incorporated by reference into the present disclosure). Unlike protein or peptide based subunit Vaccines, DNA immunization provides protective immunity through expression of foreign proteins by host cells, thus allowing the presentation of antigen to the immune system in a manner more analogous to that which occurs during infection with viruses or intracellular pathogens (ref. 2). Although considerable interest has been generated by this technique, successful immunity has been most consistently induced by DNA immunization for viral diseases (ref. 3). Results have been more variable with non-viral pathogens which may reflect differences in the nature of the pathogens, in the immunizing antigens chosen, and in the routes of immunization (ref. 4). Further development of DNA vaccination will depend on elucidating the underlying immunological mechanisms and broadening its application to other infectious diseases for which existing strategies of vaccine development have failed.

*Chlamydia trachomatis* is an obligate intracellular bacterial pathogen which usually remains localized to mucosal epithelial surfaces of the human host. Chlamydiae are dimorphic bacteria with an extracellular spore-like transmission cell termed the elementary body (EB) and an intracellular replicative cell termed the reticulate body (ref. 5). From a public health perspective, chlamydial infections are of great importance because they are significant causes of infertility, blindness and are a prevalent co-factor facilitating the transmission of human immunodeficiency virus type 1 (ref. 6). Protective immunity to *C. trachomatis* is effected through cytokines released by Th1-like CD 4 lymphocyte responses and by local antibody in mucosal secretions and is believed to be primarily directed to the major outer membrane protein (MOMP), which is quantitatively the dominant surface protein on the chlamydial bacterial cell and has a molecular mass of about 40 kDa (ref. 19).

Initial efforts in developing a chlamydial vaccine were based on parenteral immunization with the whole bacterial cell. Although this approach met with success in human trials, it was limited because protection was short-lived, partial and vaccination may exacerbate disease during subsequent infection episodes possibly due to pathological reactions to certain chlamydial antigens (ref. 8). More recent attempts at chlamydial vaccine design have been based on a subunit design using MOMP protein or peptides. These subunit vaccines have also generally failed, perhaps because the immunogens do not induce protective cellular and humoral immune responses recalled by native epitopes on the organism (ref. 9).

EP 192033 describes the provision of DNA construct for the expression, in vitro, of *Chlamydia trachomatis* MOMP polypeptides comprising the following operably linked elements:

a transcriptional promoter, a DNA molecule encoding a *C. trachomatis* MOMP polypeptide comprising a MOMP polynucleotide at least 27 base pairs in length from a sequence provided in Appendix A thereto, and a transcriptional terminator, wherein at least one of the transcriptional regulatory elements is not derived from *Chlamydia trachomatis*. There is no disclosure or suggestion in this prior art to effect DNA immunization with any such constructs.

WO 94/26900 describes the provision of hybrid picornaviruses which express chlamydial epitopes from MOMP of *Chlamydia trachomatis* and which is capable of inducing antibodies immuno-reactive with at least three different *Chlamydia serovars*. The hybrid picornavirus preferably is a hybrid polio virus which is attenuated for human administration.

WO 98/02546, assigned to the assignee hereof and the disclosure of which is incorporated herein by reference, describes the DNA immunization of a host by a plasmid vector comprising a nucleotide sequence encoding a major outer membrane protein (MOMP) of a strain of *Chlamydia* or encoding the N-terminal half of MOMP.

SUMMARY OF THE INVENTION

The present invention is concerned with nucleic acid immunization, specifically DNA immunization, to generate in a host protective antibodies to a fragment of MOMP of a strain of *Chlamydia* that encompasses epitopic sequences. DNA immunization induces a broad spectrum of immune responses including Th1-like CD4 responses and mucosal immunity.

In one aspect of the invention, there is provided a non-replicating vector, comprising a nucleotide sequence encoding a region comprising at least one of the conserved domains 2, 3 and 5 of a major outer membrane protein of a strain of *Chlamydia*, and a promoter sequence operatively coupled to the nucleotide sequence for expression of the at least one conserved domain in a host.

A MOMP gene fragment that encompasses epitopic sequences may include one or more conserved domain (CD) sequences and/or one or more variable domain (VD) sequences of MOMP from a strain of *Chlamydia*. In particular, the fragment may encompass the CD2 and VD2 sequences, CD3 and VD3 sequences and CD5 sequence. Clones containing nucleotide sequences encoding such fragments are termed clones CV2, CV3 and CD5 herein. Clone CV2 encompasses nucleotides 247 to 468 of *Chlamydia trachomatis* MOMP gene, clone CV3 encompasses nucleotides 469 to 696 of *Chlamydia trachomatis* MOMP gene and clone CV5 encompasses nucleotides 931 to 1098 of *Chlamydia trachomatis* MOMP gene. The present invention employs the conserved domains 2, 3 and 5.

The strain of *Chlamydia* may be a strain of *Chlamydia* inducing chlamydial infection of the lung, including *Chlamydia trachomatis* or *Chlamydia pneumoniae*. The non-replicating vector may be plasmid pcDNA3 into which the nucleotide sequence is inserted. The immune response which is stimulated may be predominantly a cellular immune response.

In one aspect of the present invention, there is provided an immunogenic composition for in vivo administration to a host for the generation in the host of a protective immune response to a major outer membrane protein (MOMP) of a strain of *Chlamydia*, comprising a non-replicating vector that generates a MOMP-specific immune response, and a promoter sequence operatively coupled to the nucleotide sequence for expression of the MOMP fragment in the host; and a pharmaceutically-acceptable carrier therefor.

In a further aspect of the invention, there is provided as a method of immunizing a host against disease caused by infection with a strain of *Chlamydia*, which comprises administering to the host an effective amount of a non-replicating vector as provided herein that generates a MOMP-specific immune response, and a promoter sequence operatively coupled to the nucleotide sequence for expression of the conserved sequence in the host.

In these aspects of the present invention, the various options and alternatives discussed above may be employed.

The non-replicating vector may be administered to the host, including a human host, in any convenient manner, such as intramuscularly or intranasally. Intranasal administration stimulated the strongest immune response in experiments conducted herein.

The present invention also includes, in an additional aspect thereof, a method of using a nucleotide sequence encoding a MOMP fragment that generates a MOMP-specific immune response, to produce an immune response in a host, which comprises isolating the nucleotide sequence as described above, operatively linking the nucleotide sequence to at least one control sequence to produce a non-replicating vector, the control sequence directing expression of the MOMP fragment when introduced into a host to produce an immune response to the MOMP fragment, and introducing the vector into a host.

A further aspect of the present invention provides a method of producing a vaccine for protection of a host against disease caused by infection with a strain of *Chlamydia*, which comprises isolating a nucleotide sequence encoding a MOMP fragment as described above and that generates a MOMP-specific immune response, operatively linking the nucleotide sequence to at least one control sequence to produce a non-replicating vector, the control sequence directing expression of the MOMP fragment when introduced to a host to produce an immune response to the MOMP fragment, and formulating the vector as a vaccine for in vivo administration to a host. The invention extends to the vaccine produced by this method.

Advantages of the present invention, therefore, include a method of obtaining a protective immune response to infection carried by a strain of *Chlamydia* by nucleic acid immunization of nuelcic acid sequence encoding epitopic sequences of the major outer membrane protein of a strain of *Chlamydia* that generate a MOMP-specific immune response.

BRIEF DESCRIPTION OF DRAWINGS

FIGS. 10A to 10F show a comparison of the amino acid sequence of MOMP sequences (SEQ ID NOS: 1 to 15) from a variety of serovars of *C. trachomatis*. Residues which are identical to serovar E MOMP are represented by dots. The four VDs (VDI to VDIV) and the conserved cysteines are boxed by solid line. The conserved position where one cysteine is located in all *C. trachomatis* and *C. pneumonltis* MOMP sequences, but where one serine is located in GPIC and Mn MOMPs, is boxed by a broken line. Numbers above boxes denote amino acid residues of serovar E MOMP only.

GENERAL DESCRIPTION OF THE INVENTION

Figure 1:
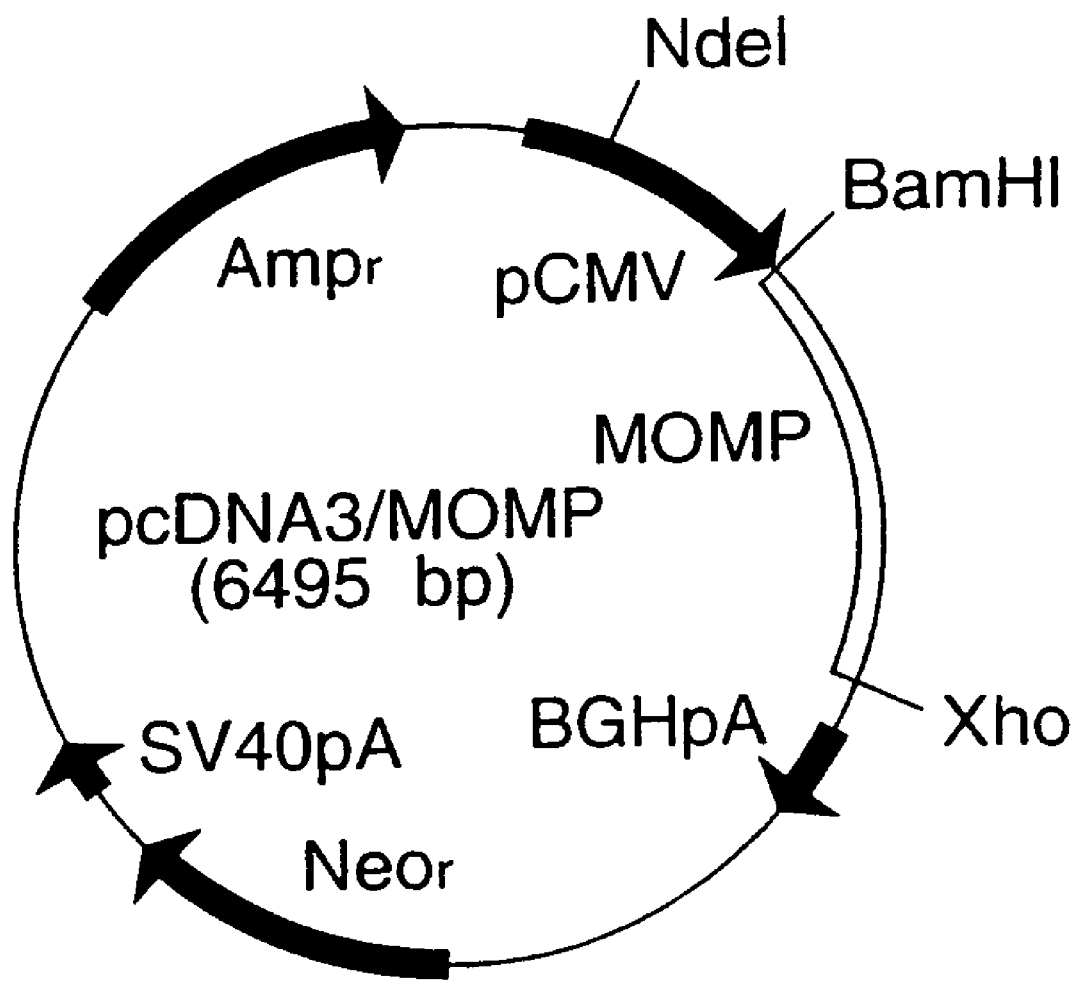
FIG. 1 shows the elements and construction of plasmid pcDNA3/MOMP, 6495 bp in size.

To illustrate the present invention, plasmid DNA was constructed containing the MOMP gene fragments from the

*C. trachomatis* mouse pneumonitis strain (MoPn), which is a natural murine pathogen, permitting experimentation to be effected in mice. It is known that primary infection in the model induces strong protective immunity to reinfection. For human immunization, a human pathogen strain is used, such as serovar C of *C. trachomatis*.

Any convenient plasmid vector may be used for the MOMP gene fragment, such as pcDNA3, a eukaryotic II-selectable expression vector (Invitrogen, San Diego, Calif., USA), containing a cytomegalovirus promoter. The MOMP gene fragment may be inserted in the vector in any convenient manner. The gene fragments may be amplified from *Chiamydia trachomatic* genomic DNA by PCR using suitable primers and the PCR product cloned into the vector. The MOMP gene-carrying plasmid may be transferred, such as by electroporation, into *E. coli* for replication therein. Plasmids may be extracted from the *E. coli* in any convenient manner.

The plasmid containing the MOMP gene fragment may be administered in any convenient manner to the host, such as intramuscularly or intranasally, in conjunction with a pharmaceutically-acceptable carrier. In the experimentation outlined below, it was found that intranasal administration of the plasmid DNA elicited the strongest immune response.

The data presented herein and described in detail below demonstrates that DNA immunization with specific *C. trachomatis* MOMP gene fragments elicits both cellular and humoral immune responses and produces significant protective immunity to lung challenge infection with *C. trachomatis* MoPn. The results are more encouraging than those obtained using recombinant MOMP protein or synthetic peptides as the immunogen and suggest that DNA immunization is an alternative method to deliver a chlamydial subunit immunogen in order to elicit the requisite protective cellular and humoral immune responses.

The data presented herein also demonstrate the importance of selection of an antigen gene fragment for DNA immunization. As described in the aforementioned WO 98/02546, the antigen gene elicits immune responses that are capable of stimulating recall immunity following exposure to the natural pathogen. In particular, injection of a DNA expression vector encoding the major outer surface protein (pMOMP) or fragment thereof but not one encoding a cytoplasmic enzyme (CTP synthetase) of *C. trachomatis*, generated significant protective immunity to subsequent chiamydial challenge. The protective immune response appeared to be predominantly mediated by cellular immunity and not by humoral immunity since antibodies elicited by DNA vaccination did not bind to native EBs. In addition, MOMP DNA but not CTP synthetase DNA immunization elicited cellular immunity readily recalled by native EBs as shown by positive DTH reactions.

In addition, as set forth in WO 98/02546, mucosal delivery of MOMP DNA is significantly more efficient in inducing protective immunity to *C. trachomatis* infection than intramuscular injection. This may be relevant to the nature of *C. trachomatis* infection which is essentially restricted to mucosal surfaces and the efficiency of antigen presentation (ref. 14). The rich population and rapid recruitment of dendritic cells into the respiratory epithelium of the lung may be relevant to the enhanced efficacy of intranasal DNA immunization experiments (ref. 15). The data presented in WO 98/02546 represents the demonstration of a first subunit chlamydial vaccine which engenders substantial protective immunity.

Additionally, it may be possible to amplify (and/or canalize) the protective immune response by co-administration of DNAs that express immunoregulatory cytokines in addition to the antigen gene in order to achieve complete immunity (ref. 21) The use of multiple antigen genes from chlamydiae may augment the level of protective immunity achieved by DNA vaccination.

Figure 2:
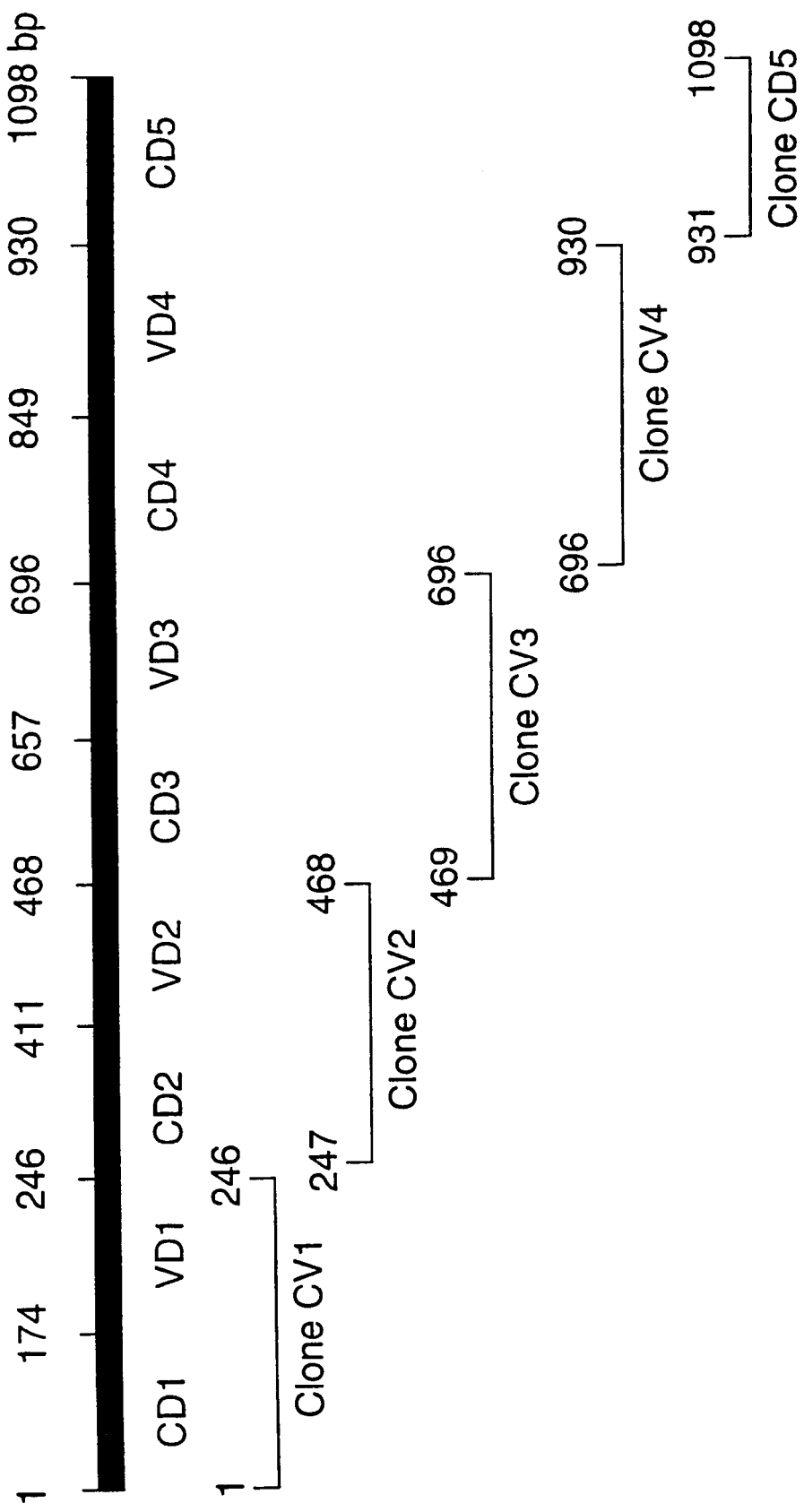
FIG. 2 shows schematically the nucleotide structure of the mature MOMP gene of *C. trachomatis* MoPn strain with conserved (CD) and variable (VD) domains identified as well as clones formed by cloning the identified sequences into pcDNA3, as described below in the Examples.
Figure 3:
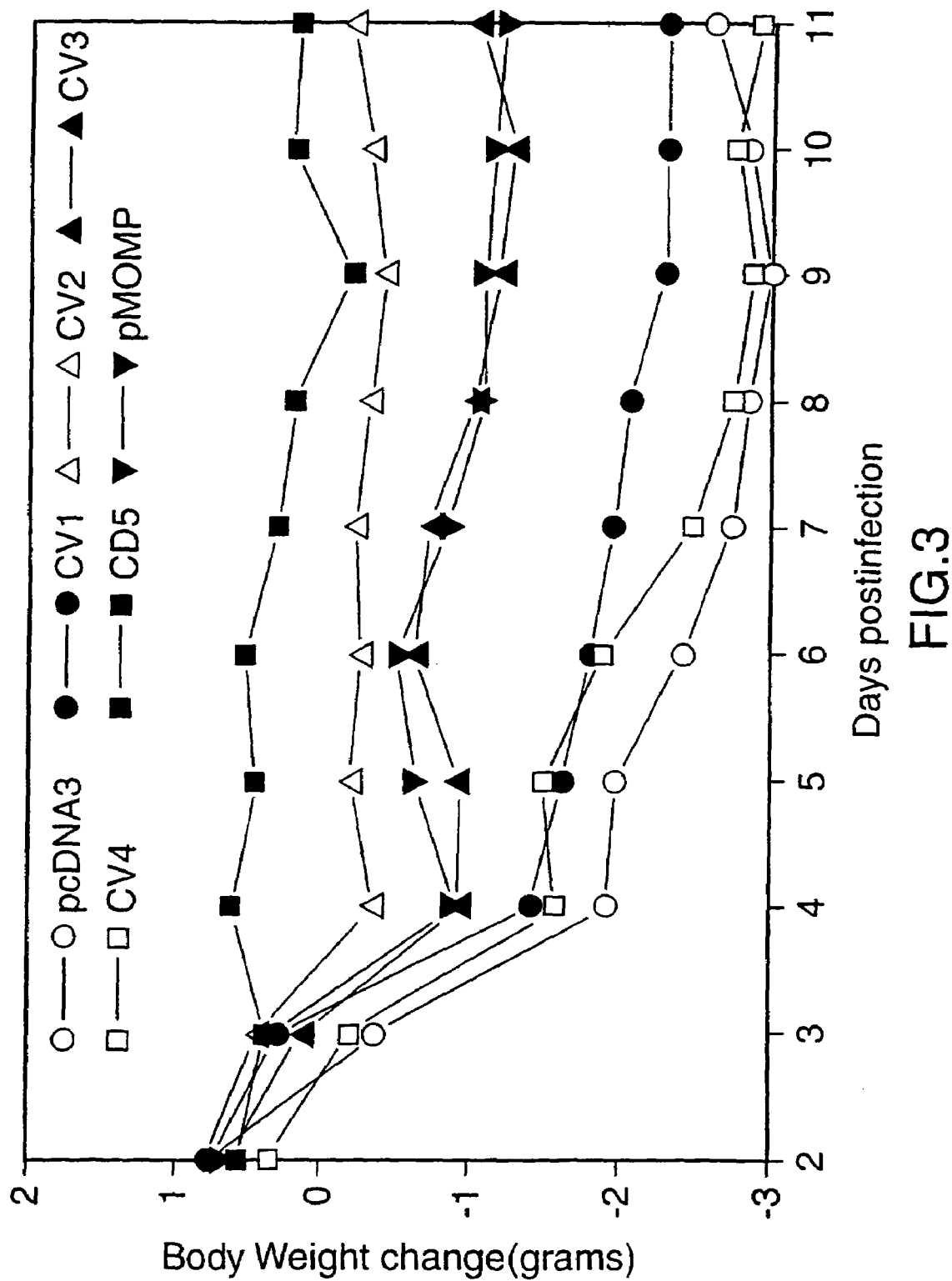
FIG. 3 shows the loss in body weight (in grams) following intranasal challenge with $5\times10^3$ IFU of MoPn among groups of Balb/c mice intramuscularly immunized with blank vector (pcDNA3), with pcDNA3 into which is individually cloned CV1 to CD5 encoding MOMP nucleotide sequences (CV1 etc.), and with pcDNA3 into which the whole MOMP encoding nucleotide sequence is cloned (pMOMP)
Figure 4:
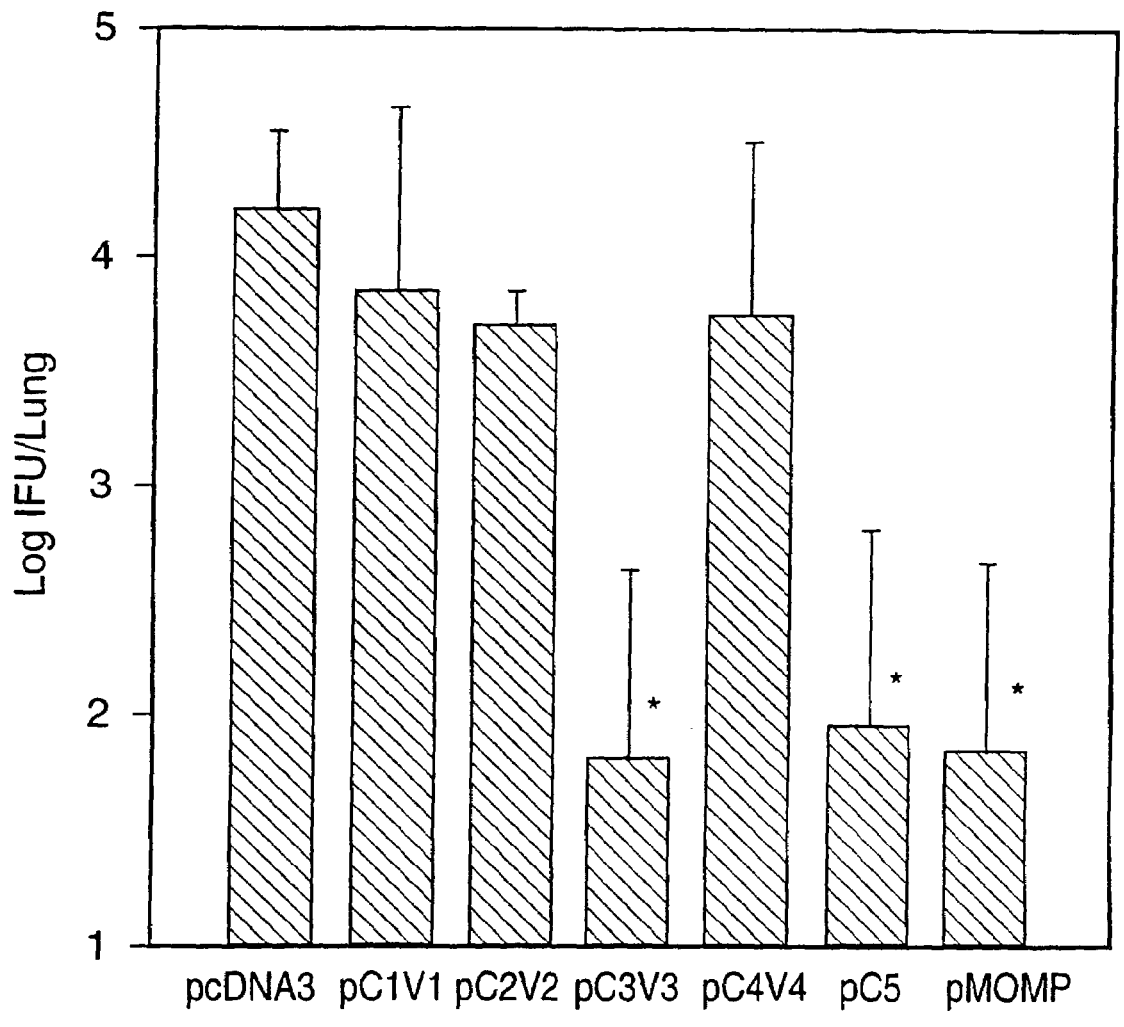
FIG. 4 shows the results of assays to determine growth of *C. trachomatis* on day 10 in lungs of mice challenged with $5\times10^3$ IFU of MoPn following intramuscular immunization with blank vector (pcDNA3), with pcDNA3 into which is individually cloned CV1 to CD5 encoding MOMP nucleotide sequences (pCV1 etc), and with pcDNA3 into which the whole MOMP encoding nucleotide sequence is cloned (pMOMP).
Figure 5:
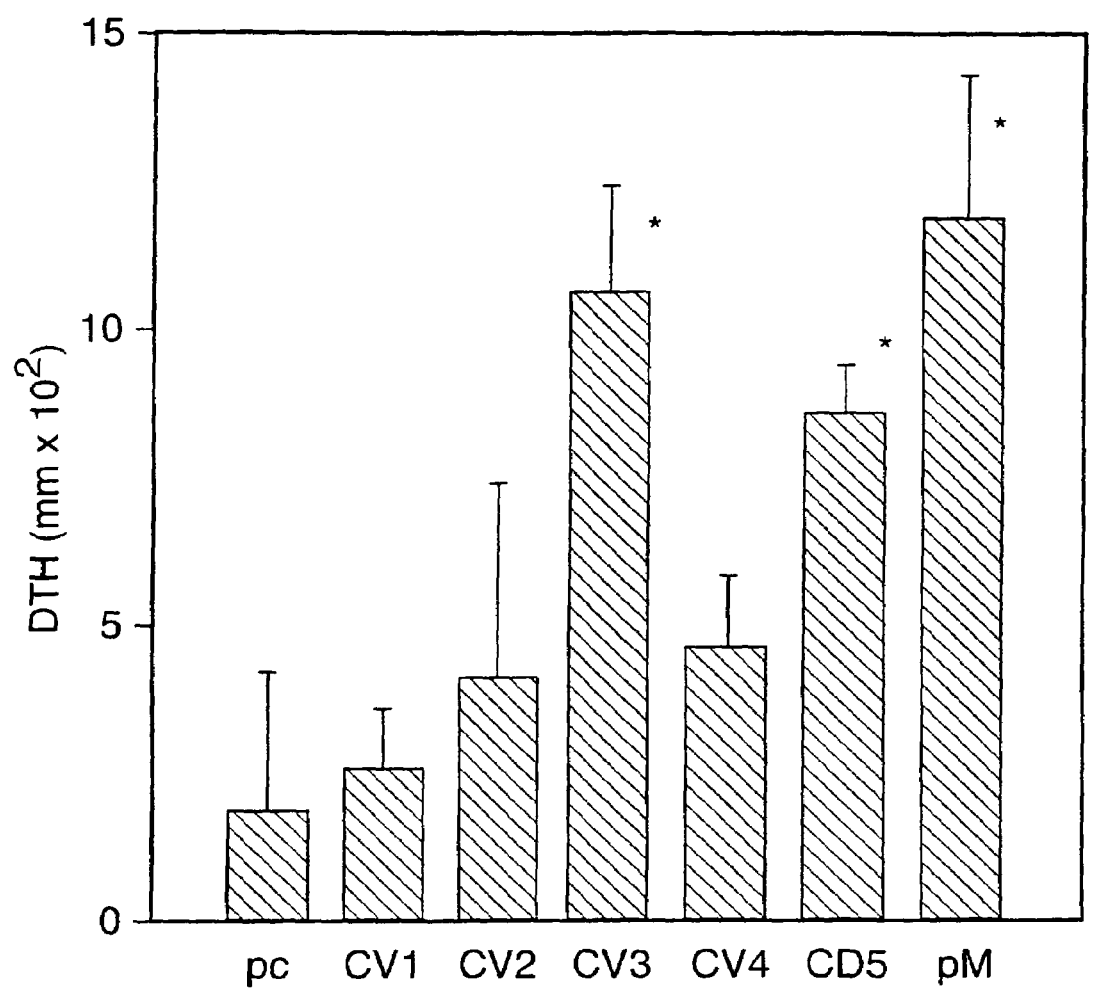
FIG. 5 shows footpad swelling reactions (DTH) 48 hours after footpad injection of $2\times10^5$ IFU of inactivated MoPn EBs among groups of Balb/c mice intramuscularly immunized with blank pcDNA3 vector (PC), with pcDNA3 into which is individually cloned CV1 to CD5 encoding MOMP nucleotide sequences (CV1 etc), and with pcDNA3 into which the whole MOMP encoding nucleotide sequence is cloned (pM).

A possible concern regarding MOMP DNA immunization according to WO 98/02546 stems from the observation that the MOMP among human *C. trachomatis* strains is highly polymorphic (ref. 16) and hence it may be difficult to generate a universal chlamydial vaccine based on this antigen gene. One way to solve this problem is to search for conserved protective epitope(s) within the MOMP molecule, as described herein. As seen in the results presented below, certain vectors containing nucleotide sequences encoding conserved and variable domains, identified in FIG. 2, or conserved domains generated a protective immune response, as determined by loss of body weight, as shown in FIG. 3. FIG. 4 shows that the pCV3 and pCD5 immunogen evoked a protective immune response to MoPn challenge as measured by in vivo growth of MoPn in lung tissue day 10 post challenge and comparable to pMOMP. FIG. 5 shows that immunization with the vectors elicited variable positive DTH responses for footpad injection of MoPn Ebs.

Figure 6:
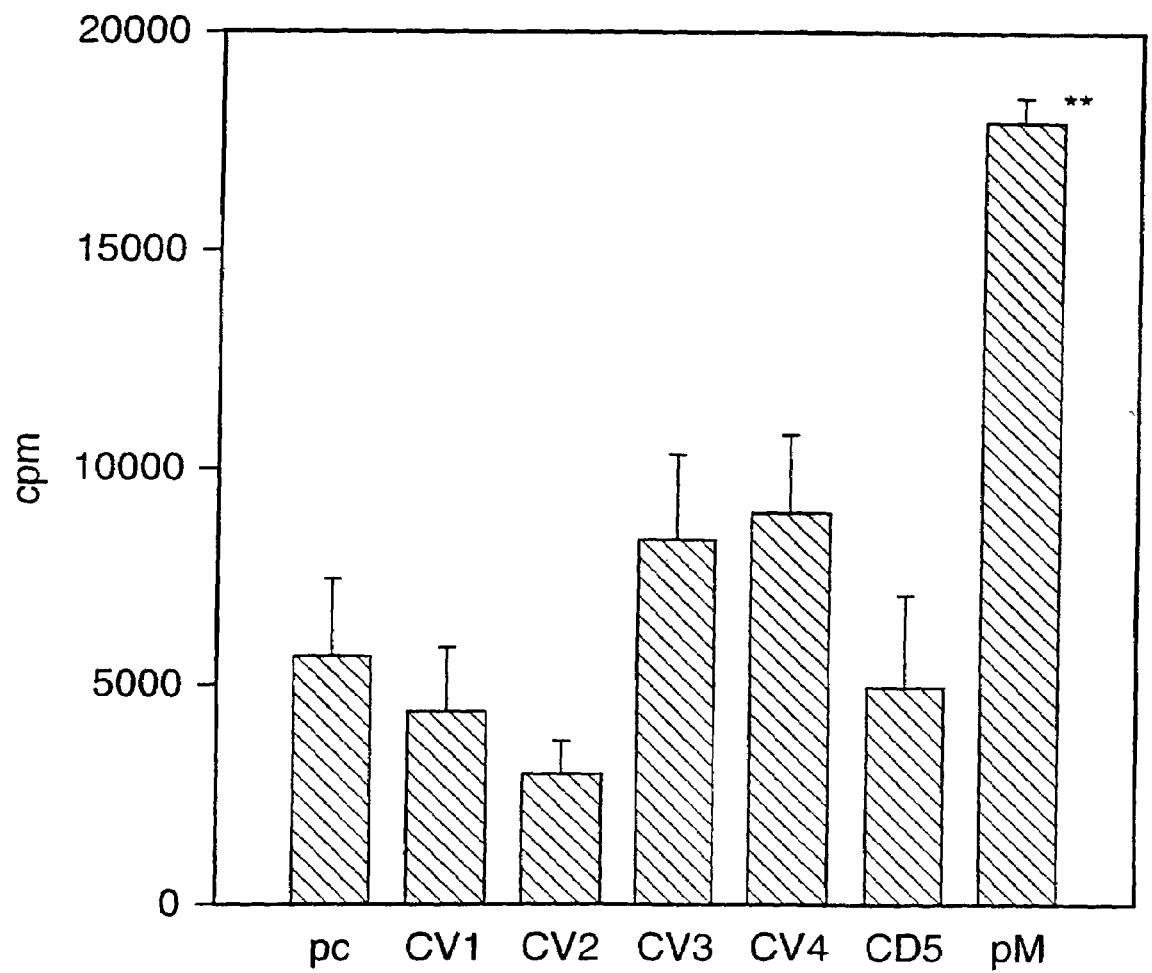
FIG. 6 shows the proliferation responses of splenocytes at day 60 post immunization after in vitro stimulation with whole inactivated MoPn EBs for 96 hours among groups of Balb/c mice immunized with blank pcDNA3 vector (pc), with pcDNA3 into which is individually cloned CV1 to CD5 encoding MOMP nucleotide sequences (CV1 etc), and with pcDNA3 into which the whole MOMP encoding nucleotide sequences is cloned (pM).
Figure 7:
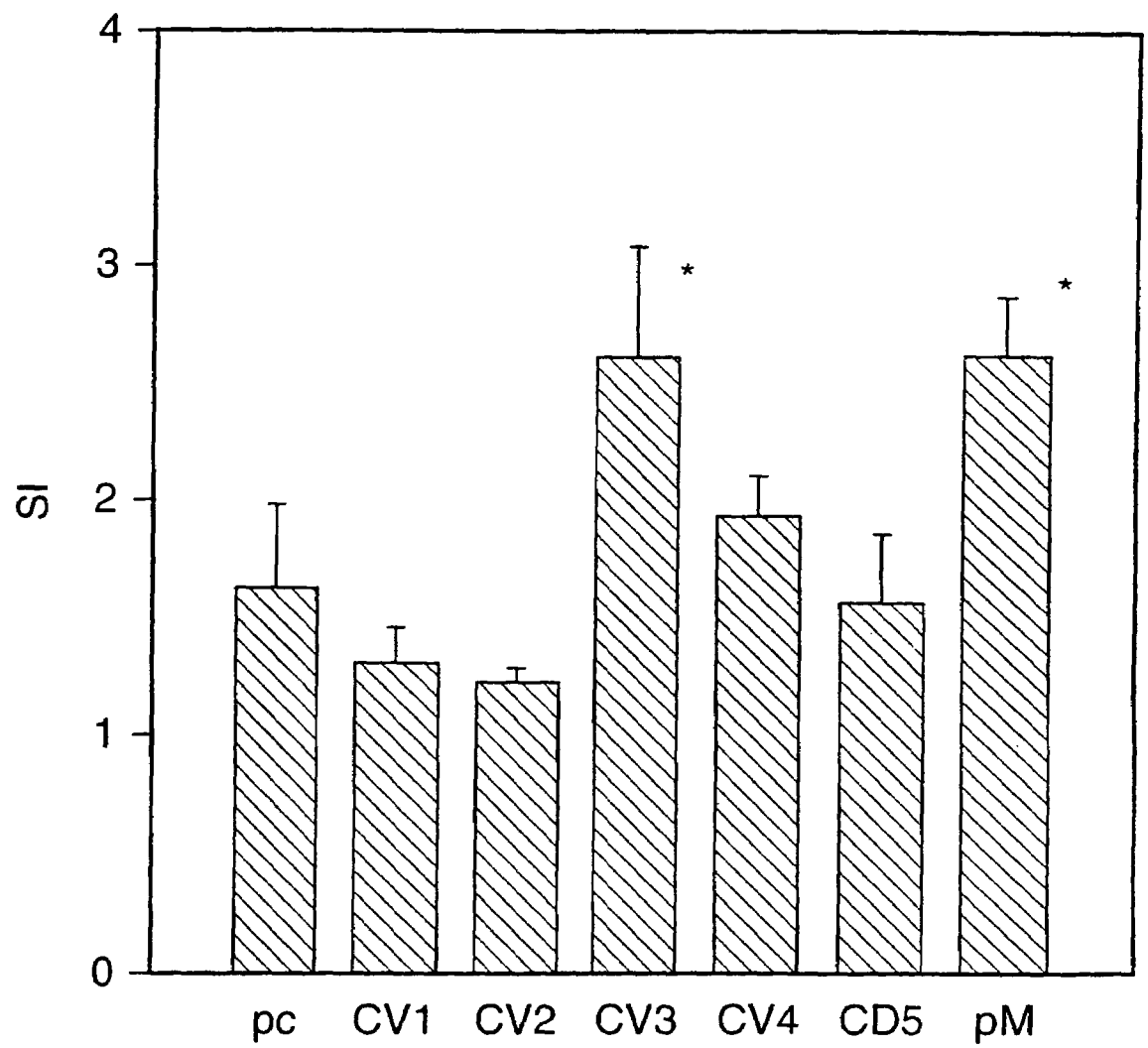
FIG. 7 shows the proliferation responses of splenocytes to the same constructs is in FIG. 6, except that the results are expressed as a stimulation index (SI).

FIGS. 6 and 7 show the proliferation responses of splenocytes to the vectors containing the conserved and variable domains and the whole MOMP gene. The results set forth in FIGS. 6 and 7 show that pCV3 and PMOMP elicit a cell mediated immune response.

Figure 8:
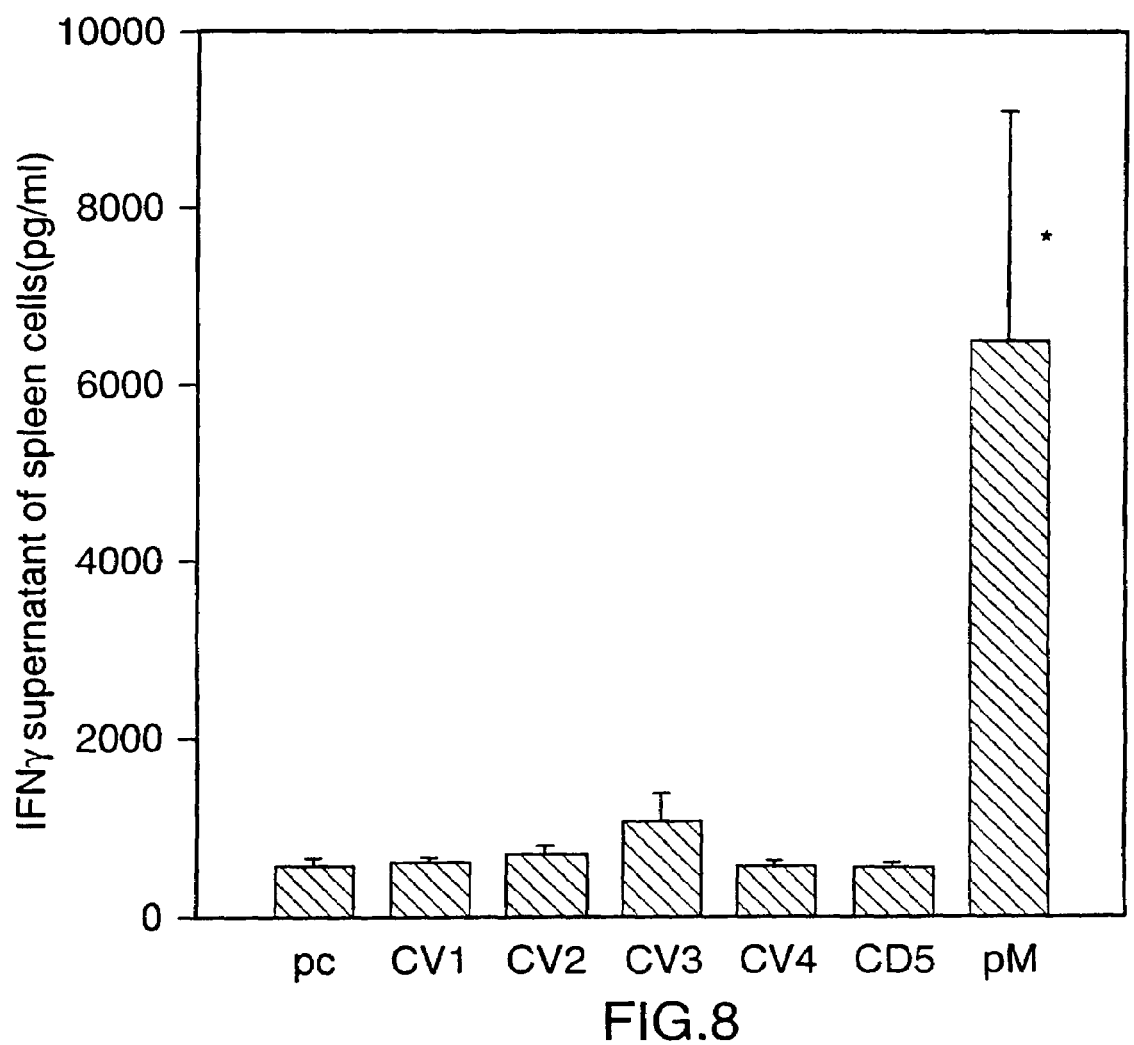
FIG. 8 shows the interferon-γ secretion response of MoPn stimulated splenocytes collected on day 60 after immunization among groups of Balb/c mice immunized with blank pcDNA3 vector (pc), with pcDNA3 into which is individually cloned CV1 to CD5 encoding MOMP nucleotide sequences (CV1 etc), and with pcDNA3 into which the whole MoPn MOMP encoding nucleotide sequence is cloned (pM).

FIG. 8 shows interferon-γ secretion responses of the splenocytes to the vectors containing the conserved and variable domains and the whole MOMP gene. The results obtained in FIG. 8 suggest that cytokine generation may not necessarily be a correlate of a protective immune response.

Another, possibly more feasible, way is to design a multivalent vaccine based on multiple MOMP genes. The latter approach is justified by the fact that the inferred amino acid sequences of MOMP among related serovars is relatively conserved (see Figures 10A to 10F) and the repertoire of *C. trachomatis* gene variants appears to be finite (ref. 16).

It is clearly apparent to one skilled in the art, that the various embodiments of the present invention have many applications in the fields of vaccination, diagnosis and treatment of chlamydial infections. A further non-limiting discussion of such uses is further presented below.

1. Vaccine Preparation and Use

Immunogenic compositions, suitable to be used as vaccines, may be prepared from the MOMP gene fragments thereof and vectors as disclosed herein. The vaccine elicits an immune response in a subject which includes the production of anti-MOMP antibodies. Immunogenic compositions, including vaccines, containing the nucleic acid may be prepared as injectables, in physiologically-acceptable liquid solutions or emulsions for polynucleotide administration. The nucleic acid may be associated with liposomes, such as lecithin liposomes or other liposomes known in the art, as a nucleic acid liposome (for example, as described in WO 93/24640) or the nucleic acid may be associated with an adjuvant, as described in more detail below. Liposomes comprising cationic lipids interact spontaneously and rapidly with polyanions, such as DNA and RNA, resulting in liposome/nucleic acid complexes that capture up to 100% of the polynucleotide. In addition, the polycationic complexes fuse with cell membranes, resulting in an intracellular delivery of polynucleotide that bypasses the degradative enzymes of the lysosomal compartment. WO 94/27435 describes compositions for genetic immunization comprising cationic lipids and polynucleotides. Agents which assist in the cellular uptake of nucleic acid, such as calcium ions, viral proteins and other transfection facilitating agents, may advantageously be used.

Polynucleotide immunogenic preparations may also be formulated as microcapsules, including biodegradable time-release particles. Thus, U.S. Pat. No. 5,151,264 describes a particulate carrier of a phospholipid/glycolipid/polysaccharide nature that has been termed Bio Vecteurs Supra Moleculaires (BVSM). The particulate carriers are intended to transport a variety of molecules having biological activity in one of the layers thereof.

U.S. Pat. No. 5,075,109 describes encapsulation of the antigens trinitrophenylated keyhole limpet hemocyanin and staphylococcal enterotoxin B in 50:50 poly (DL-lactideco-glycolide). Other polymers for encapsulation are suggested, such as poly(glycolide), poly(DL-lactide-co-glycolide), copolyoxalates, polycaprolactone, poly(lactide-co-caprolactone), poly(esteramides), polyorthoesters and poly(8-hydroxybutyric acid), and polyanhydrides.

WO 91/06282 describes a delivery vehicle comprising a plurality of bioadhesive microspheres and antigens. The microspheres being of starch, gelatin, dextran, collagen or albumin. This delivery vehicle is particularly intended for the uptake of vaccine across the nasal mucosa. The delivery vehicle may additionally contain an absorption enhancer.

The MOMP gene fragment containing non-replicating vectors may be mixed with pharmaceutically acceptable excipients which are compatible therewith. Such excipients may include, water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof. Immunogenic compositions and vaccines may be administered parenterally, by injection subcutaneously, intravenously, intradermally or intramuscularly, possibly following pretreatment of the injection site with a local anesthetic. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories and oral formulations may be desirable. For suppositories, binders and carriers may include, for example, polyalkylene glycols or triglycerides. Oral formulations may include normally employed incipients, such as, for example, pharmaceutical grades of saccharine, cellulose and magnesium carbonate.

The immunogenic preparations and vaccines are administered in a manner compatible with the dosage formulation, and in such amount as will be therapeutically effective, protective and immunogenic. The quantity to be administered depends on the subject to be treated, including, for example, the capacity of the individual's immune system to synthesize the MOMP and antibodies thereto, and if needed, to produce a cell-mediated immune response. Precise amounts of active ingredient required to be administered depend on the judgement of the practitioner. However, suitable dosage ranges are readily determinable by one skilled in the art and may be of the order of about 1 µg to about 1 mg of the MOMP gene-containing vectors. Suitable regimes for initial administration and booster doses are also variable, but may include an initial administration followed by subsequent administrations. The dosage may also depend on the route of administration and will vary according to the size of the host. A vaccine which protects against only one pathogen is a monovalent vaccine. Vaccines which contain antigenic material of several pathogens are combined vaccines and also belong to the present invention. Such combined vaccines contain, for example, material from various pathogens or from various strains of the same pathogen, or from combinations of various pathogens.

Immunogenicity can be significantly improved if the vectors are co-administered with adjuvants, commonly used as 0.05 to 0.1 percent solution in phosphate-buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Thus, adjuvants have been identified that enhance the immune response to antigens. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines.

A wide range of extrinsic adjuvants and other immuno-modulating material can provoke potent immune responses to antigens. These include saponins complexed to membrane protein antigens to produce immune stimulating complexes (ISCOMS), pluronic polymers with mineral oil, killed mycobacteria in mineral oil, Freund's complete adjuvant, bacterial products, such as muramyl dipeptide (MDP) and lipopolysaccharide (LPS), as well as Quil A derivatives and components thereof, QS 21, calcium phosphate, calcium hydroxide, zinc hydroxide, an octodecyl ester of an amino acid, ISCOPREP, DC-chol, DDBA and polyphosphazene. Advantageous combinations of adjuvants are described in copending U.S. patent application Ser. No. 08/261,194 filed Jun. 16, 1994 and Ser. No. 08/483,856 filed Jun. 7, 1995, assigned to the assignee hereof and the disclosures of which are incorporated herein by reference thereto (WO 95/34308).

In particular embodiments of the present invention, the non-replicating vector comprising a first nucleotide sequence encoding a MOMP gene fragment of *Chlamydia* may be delivered in conjunction with a targeting molecule to target the vector to selected cells including cells of the immune system.

The non-replicating vector may be delivered to the host by a variety of procedures, for example, Tang et al. (ref. 17) disclosed that introduction of gold microprojectiles coated with DNA encoding bovine growth hormone (BGH) into the skin of mice resulted in production of anti-BGH antibodies in the mice, while Davis et al. (ref. 18) showed that a jet injector could be used to transfect skin, muscle, fat and mammary tissues of living animals.

2. Immunoassays

The MOMP gene fragments and vectors of the present invention also are useful as immunogens for the generation of anti-MOMP antibodies for use in immunoassays, including enzyme-linked immunosorbent assays (ELISA), RIAs and other non-enzyme linked antibody binding assays or procedures known in the art. In ELISA assays, the non-replicating vector first is administered to a host to generate antibodies specific to the MOMP. These MOMP specific antibodies are immobilized onto a selected surface, for example, a surface capable of binding the antibodies, such as the wells of a polystyrene microtiter plate. After washing to remove incompletely adsorbed antibodies, a nonspecific protein, such as a solution of bovine serum albumin (BSA) that is known to be antigenically neutral with regard to the test sample, may be bound to the selected surface. This allows for blocking of nonspecific adsorption sites on the immobilizing surface and thus reduces the background caused by nonspecific bindings of antisera onto the surface.

The immobilizing surface is then contacted with a sample, such as clinical or biological materials, to be tested in a manner conducive to immune complex (antigen/antibody) formation. This procedure may include diluting the sample with diluents, such as solutions of BSA, bovine gamma globulin (BGG) and/or phosphate buffered saline (PBS)/Tween. The sample is then allowed to incubate for from about 2 to 4 hours, at temperatures such as of the order of about 20° to 37° C. Following incubation, the sample-contacted surface is washed to remove non-immunocomplexed material. The washing procedure may include washing with a solution, such as PBS/Tween or a borate buffer. Following formation of specific immunocomplexes between the test sample and the bound MOMP specific antibodies, and subsequent washing, the occurrence, and even amount, of immunocomplex formation may be determined.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

Example 1

This Example illustrates the preparation of a plasmid vector containing the MOMP gene, as also described in WO 98/02546.

PMOMP expression vector was made as follows. The MOMP gene was amplified from *Chlamydia trachomatis* mouse pneumonitis (MoPn) strain genomic DNA by polymerase chain reaction (PCR) with a 5' primer (GGGGATCCGCCACCATGCTGCCTGTGGGGAATCCT) (SEQ ID NO: 16) which includes a BamH1 site, a ribosomal binding site, an initiation codon and the N-terminal sequence of the mature MOMP of MoPn and a 3' primer (GGGGCTCGAGCTATTAACGGAACTGAGC) (SEQ ID NO: 17) which includes the C-terminal sequence of the MoPn MOMP, a Xho1 site and a stop codon. The DNA sequence of the MOMP leader peptide gene sequence was excluded. After digestion with BamH1 and Xhol, the PCR product was cloned into the pcDNA3 eukaryotic II-selectable expression vector (Invitrogen, San Diego) with transcription under control of the human cytomegatovirus major intermediate early enhancer region (CMV promoter). The MOMP gene-encoding plasmid was transferred by electroporation into *E. coli* DH5αF which was grown in LB broth containing 100 µg/ml of ampicillin. The plasmids was extracted by Wizard™ Plus Maxiprep DNA purification system (Promega, Madison). The sequence of the recombinant MOMP gene was verified by PCR direct sequence analysis, as described (ref. 20). Purified plasmid DNA was dissolved in saline at a concentration of 1 mg/ml. The DNA concentration was determined by a DU-62 spectrophotometer (Beckman, Fullerton, Calif.) at 260 nm and the size of the plasmid was compared with DNA standards in ethidium bromide-stained agarose gel.

The MOMP gene containing so obtained plasmid, pcDNA3/MOMP, and its constitutive elements are shown in FIG. 1. A similar plasmid (pM(C)) was constructed from the MOMP gene serovar C of *C. trachomatis*.

For experimental design, groups of 4 to 5 week old female Balb/c mice (5 to 13 per group) were immunized intramuscularly (IM) or intranasally (IN) with plasmid DNA containing the coding sequence of the MoPn MOMP gene (1095 bp), prepared as described in Example 1, or with the coding sequence of the *C. trachomatis* serovar $L_2$ CTP synthetase gene (1619 bp (refs. 10, 12), prepared by a procedure analogous described in Example 1. CTP synthetase is a conserved chlamydial cytoplasmic enzyme catalyzing the final step in pyrimidine biosynthesis and is not known to induce protective immunity. Negative control animals were injected with saline or with the plasmid vector lacking an inserted chlamydial gene.

Example 2

This Example illustrates DNA immunization of mice and the results of DTH testing.

A model of murine pneumonia induced by the *C. trachomatis* mouse pneumonitis strain (MoPn) was used (ref. 11). Unlike most strains of *C. trachomatis* which are restricted to producing infection and disease in humans, MoPn is a natural murine pathogen. It has previously been demonstrated that primary infection in this model induces strong protective immunity to reinfection. In addition, clearance of infection is related to CD4 Th1 lymphocyte responses and is dependent on MHC class II antigen presentation (ref. 11).

For IM immunization, both quardiceps were injected with 100 µg DNA in 100 µl of saline per injection site on three occasions at 0, 3 and 6 weeks. For IN immunization, anaesthetized mice aspirated 25 µl of saline containing 50 µg DNA on three occasions at 0, 3 and 6 weeks. As a positive control, a separate group of mice received $5 \times 10^6$ inclusion forming units (IFUs) of MoPn EBs administered intraperitoneally in incomplete Freund's adjuvant according to the above schedule. At week 8, all groups of mice had sera collected for measuring antibodies and were tested for delayed-type hypersensitivity (DTH) to MoPn Ebs by footpad injection (ref. 13).

A positive 48 and 72 hour DTH reaction was detected among mice immunized with MOMP DNA or with MoPn Ebs but not among mice immunized with the blank vector (see FIG. 1 of WO 98/02546). The DTH reaction elicited with MOMP DNA delivered intranasally was comparable to that observed among mice immunized with EBs. No DTH reaction was detected among the groups of mice vaccinated with CTP synthetase DNA (see Table 1 below). Thus, injection of MOMP DNA generated a DTH reaction that was capable of recall by naturally processed peptides from *C. trachomatis* EBs while injection of CTP synthetase DNA failed to do so.

Example 3

This Example illustrates DNA immunization of mice and the generation of antibodies.

Injection of CTP synthetase DNA as described in Example 2 resulted in the production of serum antibodies to recombinant CTP synthetase (Table 1) (ref. 14). Antigen-specific serum Abs were measured by ELISA. Flat-bottom 96-well plates (Corning 25805, Corning Science Products, Corning, N.Y.) were coated with either recombinant chlamydial CTP-synthetase (1 µg/ml) or purified MoPn EBs ($6\times10^4$ IFU/well) overnight at 4° C. The Plates were rinsed with distilled water and blocked with 4% BSA PBS-Tween and 1% low fat skim milk for 2 hours at room temperature. Dilutions of sera samples were performed in 96-well round bottom plates immediately prior to application on the antigen coated plates. The plates were incubated overnight at 4° C. and washed ten times. Biotinylated goat anti-mouse IgG1 or goat anti-mouse IgG2a (Southern Biotechnology Associates, Inc. Birmingham, Ala.) were next applied for 1 hour at 37° C. After washing, streptoavidin-alkaline phosphatase conjugate (Jackson ImmunoResearch Laboratories, Inc. Mississagua, Ontario, Canada) were added and incubated at 37° C. for 30 min. Following another wash step, phosphatase substrate in phosphatase buffer (pH 9.8) was added and allowed to develop for 1 hour. The plates were read at 405 nm on a BIORAD 3550 microplate reader.

IgG2a antibody titers were approximately 10-fold higher than lgG1 antibody titers suggesting that DNA immunization elicited a more dominant $T_{H1}$-like response. Injection of MOMP DNA as described in Example 2 resulted in the production of serum antibodies to MOMP (Table 2) as detected in an immunoblot assay (FIG. 2 of WO 98/02546). However, neither CTP synthetase DNA nor MOMP DNA immunized mice produced antibodies that bound to native *C. trachomatis* EBs (Table 1), suggesting that the antibody responses may not to be the dominantly protective mechanism.

Example 4

This Example illustrates DNA immunization of mice to achieve protection.

To investigate whether a cell-mediated immune response elicited by MOMP DNA was functionally significant, in vivo protective efficacy was evaluated in mice challenged intranasally with $1\times10^3$ IFU of *C. trachomatis* MoPn. To provide a measure of *Chlamydia*-induced morbidity, the loss in body weight was measured over 10 days following challenge with *C. trachomatis*. Mice injected with the unmodified vector were used as negative controls and mice immunized with EBs were used as positive controls. Mice immunized with MOMP DNA intranasally maintained a body weight comparable to that observed among EB immunized mice. Mice intramuscularly immunized with MOMP DNA lost body mass but did so at a rate less than the negative control group.

A more direct measure of the effectiveness of DNA vaccination is the ability of mice immunized with MOMP DNA to limit the in vivo growth of *Chlamydia* following a sublethal lung infection. Day 10 post-challenge is the time of peak growth (ref. 13) and was chosen for comparison of lung titers among the various groups of mice. Mice intranasally immunized with MOMP DNA had chlamydial lung titers that were over 1000-fold lower ($\log_{10}$ IFU 1.3±0.3; mean±SEM) than those of control mice immunized with the blank vector ($\log_{10}$ IFU 5.0±0.3; p<0.01). Mice intramuscularly immunized with MOMP DNA had chlamydial lung titers that were more than 10-fold lower than the unmodified vector group (p=0.01). Mice intranasally immunized with MOMP DNA had significantly lower chlamydial lung titers than mice immunized with MOMP DNA intramuscularly ($\log_{10}$ IFU 1.3±0.8 versus $\log_{10}$ IFU 0.66±0.3 respectively; p=0.38). The substantial difference (2.4 logs) in chlamydial lung titers observed between the intranasally and intramuscularly MOMP DNA immunized mice suggests that mucosal immunization is more efficient at inducing immune responses to accelerate chlamydial clearance in the lung. The lack of protective effect with the unmodified vector control confirms that DNA per se was not responsible for the immune response. Moreover, the absence of protective immunity following immunization with CTP synthetase DNA confirms that the immunity was specific to the MOMP DNA (see Table 1).

Example 5

This Example describes the construction of plasmids containing fragments of MOMP DNA.

A series of vectors was generated following the procedure outlined in Example 1 containing fragments of the nucleotide sequence of the MoPn MOMP gene by PCR cloning and subsequent cloning into the vector pcDNA3 to generate plasmids pCV1, pCV2, pCV3, pCV4 and pCD5, respectively, containing the respective fragments of the MoPn MOMP gene shown in FIG. 2.

Example 5:

This Example illustrates immunization of mice with pCV1, pCV2, pCV3, pCV4 and pCD5.

Balb/c mice were immunized in the quadriceps three times at three week intervals with 100 μg of pCV1, pCV2, pCV3, pGV4 and pCD5 DNA, following the procedure described in Example 2.

Fifteen days after the last immunization and 60 days after the first injection, mice were bled for measurement of serum antibodies of MoPn EBs in an EIA assay and were injected in the footpad with 25 μl ($5\times10^4$ inclusion forming units) of heat killed EBs for measurement of DTH which was measured at 72 hours (ref. 13). Mice were intranasally challenged with 1000 infectious units of MoPn and their body weight measured daily for the subsequent 10 days. At that time, mice were sacrificed and quantitative cultures of MoPn in the lung determined (ref. 13).

FIG. 3 shows that pCV2, pCV3 and pCD5 immunization evoked a protective immune response to MoPn challenge as measured by loss in body weight post infection comparable to that in mice protected against disease. FIG. 4 shows that pCV3 and pCD5 immunization evoked a protective immune response to MoPn challenge as measured by in vivo growth of MoPn in lung tissue, comparable to pMOMP.

However, the specific domains eliciting these immune responses do not include those predicted in the art to contain T-cell epitopes. In this regard, several groups have attempted to define MOMP T-cell epitopes (refs. 22 to 26). All of those studies used overlapping synthetic peptides to various regions of the MOMP protein to prime mice. None of the predicted epitopes fall within regions that have been found to be protective.

FIG. 5 shows that immunization with pCV1, pCV2, pCV3, pCV4 and pCD5 elicited variable positive DTH responses to footpad injection of MoPn EBs. pCV3 and pCD5 elicited greater responses, comparable to pMOMP.

Immunization with the unmodified vector elicited neither serum antibodies nor a DTH response.

Figure 9:
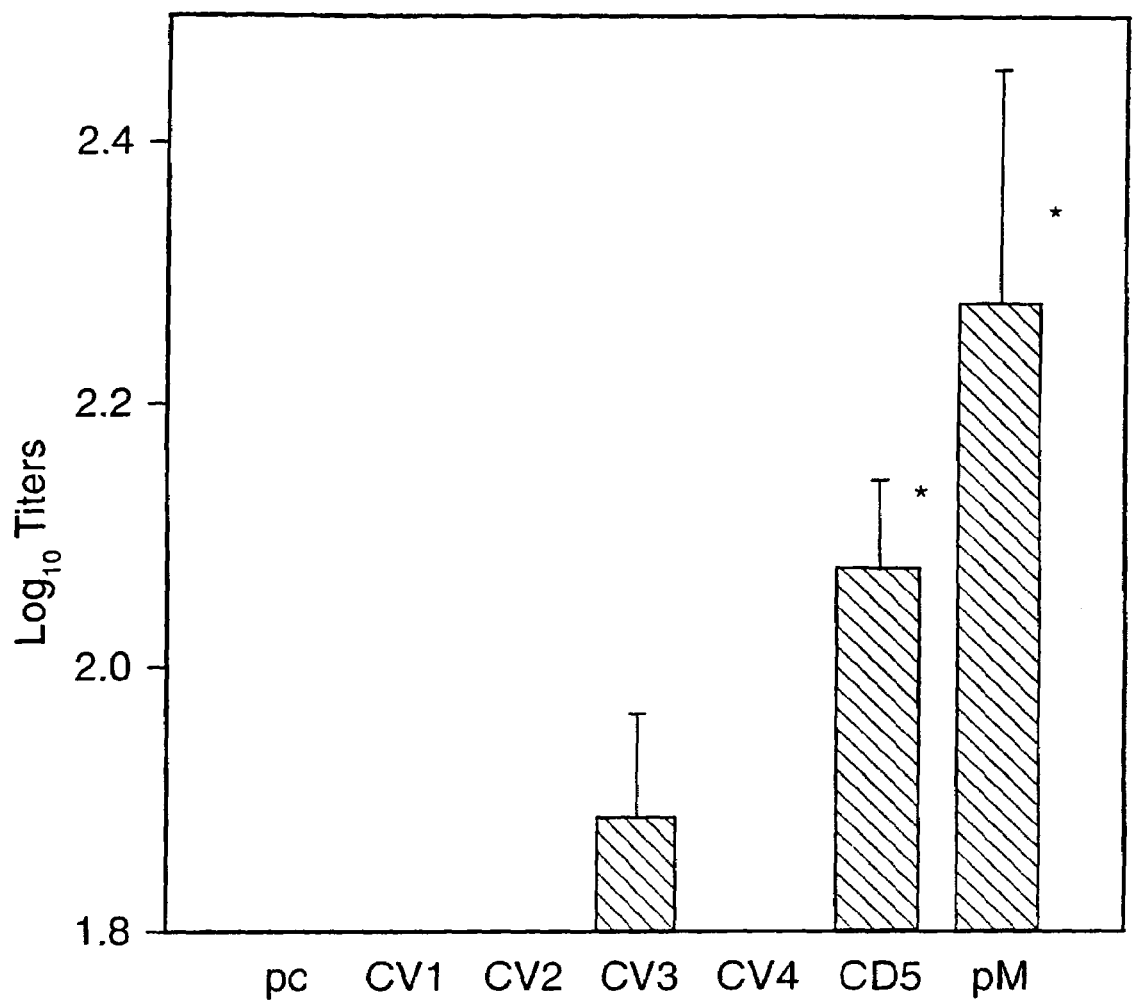
FIG. 9 shows the IgG2a antibody titer to whole MoPn EBs using sera collected at day 60 after immunization among groups of Balb/c mice immunized with blank pcDNA3 vector (pc), with pcDNA3 into which is individually cloned CV1 to CD5 encoding MOMP nucleotide sequences (CV1 etc), and with pcDNA3 into which the whole MOMP encoding nucleotide sequences is cloned (pM).

FIG. 9 shows $IgG_{2a}$ antibody titers in sera collected from the mice 60 days post immunization by the vectors containing the conserved and variable domains and full length MOMP gene. Only in the case of immunization by pCV3 and pCD5, was an $IgG_{2a}$ immune response generated, indicating that a Th1-like response was elicited by these vectors.

As may be seen in this Example, the vectors containing specific segments of the MOMP gene were able to protect against disease, based on body weight loss, namely pCV2 and pCD5. In addition, vectors pCV3 and pCD5 were able to protect against infection, based on lung titres.

Example 6

This Example illustrates the proliferation response of splenocytes to the vectors PMOMP, pCV1, pCV2, pCV3, pCV4 and pCD5.

Mice were sacrificed two weeks after the fourth immunization following the protocol of Example 2. The spleens were removed and single-cell suspensions were prepared. 200 µl of the cell suspension ($5 \times 10^5$ well) in RPMI-1640 medium containing 10% heat-inactivated fetal calf serum (FCS), 1% L-glutamine and $5 \times 10^{-5}$ M 2-mercaptoethanol (2ME, Kodak, Rochester, N.Y.) were incubated with $1 \times 10^5$ IFU/ml of MoPn in 96 well flat bottom plates in triplicate 37° C. in 5% $CO_2$ for 96 hours. Negative control wells contained spleen cells without antigen and positive control wells contained spleen cells with 0.25 µg/ml of concanavalin A. 0.25 µCi/well of tritiated ($^3H$) thymidine (2 Ci/mmol, 74 Gbq/mmol, imCi/ml, ICN, Irvine, Calif.) was added after 3 days of culture and 16h before harvest. The cells were harvested with a PHD cell harvester (Cambridge Technology Inc., Watertown, Mass., USA) and counted in 2 ml of scintillation solution (Universal, ICN, Costa Mesa) in a Beckman LS5000 counter (Beckman Instrument, UK).

As may be seen in the results presented into FIGS. 6 and 7, pCV3 and pMOMP elicited a cell-mediated immune response.

Example 7

This Example illustrates the interferon-γ secretion responses of splenocytes to the vectors pMOMP, pCV1, pCV2, pCV3, pCV4 and pCD5.

A cytokine-specific ELISPOT assay was used for the quantification of murine IFNγ and IL-10 secreting cells in the murine spleen. For all assays 96-well nitrocellulose-based microtiters (Milititer Multiscreen HA plates, Millipore Corp, Molshem, France) were coated overnight at 4° C. with 100 µl of the anti-cytokine mAb diluted in PBS at a concentration of 5 µg/ml. After removing the coating solution from the plates, wells were blocked for at least 1 hour with RPMI-1640 media containing 40% fetal calf serum at 37° C., in $CO_{2\_}$. After rinsing the plates with PBS-T once, the testing cells were added into the wells.

For induction of antigen specific IFNγ secreting cells in immunized mice, single cells were adjusted to $5 \times 10^6$ cells/ml and cultured with $2 \times 10^5$ IFU/ml of UV-killed EB of MoPn in 24 well plates for 72 hours. After washing with RPMI 1640, cells were added onto the 96-well plates for 72 hours. After washing with RPMI 1640, cells were added onto the 96-well nitrocellulose-based microtiter plates which had been previously coated with anti-cytokine antibodies. The cells were added to individual wells ($2 \times 10^5$ or $1 \times 10^5/100$-µl/well) and incubated for 24 hours at 37° C. in a $CO_2$ incubator. Wells were rinsed extensively with PBS-T containing 1% BSA. Following rinsing with PBS-T three times (removing the supporting manifold and washing the back of the plate thoroughly with PBS-T), alkaline phosphatase conjugated streptavidin in PBS containing 1% BSA at 1:2000 at a concentration of 0.5 µg/ml was added and incubated at 37° C. in $CO_2$ for 45 min. After rinsing thoroughly, 100µl/well of the colormetric substrate phosphate BICP (5-bromo-4-chloro-3-indolyl phosphate)/NBT (Nitro blue tetrazolium) at 0.16 mg/ml BICP and 1 mg/ml NBT in substrate buffer (0.1 M NaCl, 0.1M Tris, pH 9.5, 0.05 M $MgCl_2$) was added and incubated at room temperature until spots were visualized. The reaction was stopped by the addition of water.

The results obtained are set forth in FIG. 8 and suggest that cytokine generation may not necessarily be a correlate of a protective immune response.

SUMMARY OF DISCLOSURE

In summary of this disclosure, the present invention provides a method of nucleic acid, including DNA, immunization of a host, including humans, against disease caused by infection by a strain of *Chlamydia*, specifically *C. trachomatis*, employing a non-replicating vector, specifically a plasmid vector, containing a nucleotide sequence encoding an epitopic fragment of a major outer membrane protein (MOMP) of a strain of *Chlamydia* which generates a MOMP-specific immune response, and a promoter to effect expression of the MOMP fragment in the host. Modifications are possible within the scope of this invention.

TABLE 1

Serum antibody titers and delayed-type hypersensitivity (DTH) responses and in vivo growth of *Chlamydia trachomatis* following pCTP synthetase or MoPn EB immunization. Results are presented as means ± SEM.

| | Anti-MoPn EB antibodies ($log_{10}$) | | anti-rCTP synthetase antibodies ($log_{10}$) | | Anti-EB DTH | $log_{10}$ IFU/lung d10 post |
|---|---|---|---|---|---|---|
| | IgG1 | IgG2a | IgG1 | IgG2a | (mm × $10^2$) | challenge |
| Saline (n = 9) | <2 | <2 | <2 | <2 | 4.5 ± 1.5 | 4.9 ± 2.4 |
| pCTP synthetase (n = 11) | <2 | <2 | 3.8 ± .3 | 4.7 ± .1 | 1.4 ± 1.5 | 4.7 ± .13 |
| EB (n = 4) | 5.0 ± .3 | 4.8 ± .3 | 3.6 ± .8 | 2.9 ± 0 | 15.2 ± 2.0 | 0 |

TABLE 2

Serum antibody Elisa titers to *Chlamydia trachomatis* mouse pneumonitis recombinant MOMP and EBs were measured 60 days after the initial immunization among mice immunized with blank vector alone (pcDNA3), vector containing the MOMP gene (pMOMP) and vector containing the CTP synthetase gene (pCTP). Non-immunized mice were also tested.

| Immunogen | rMOMP | | EB | |
|---|---|---|---|---|
| | IgG2a | IgG1 | IgG2a | IgG1 |
| pcDNA3 | <2.6* | <2.6 | <2.6 | <2.6 |
| pMOMP | 3.77 ± 0.1 | 2.90 ± 0.14 | 3.35 ± 0.11 | <2.6 |
| pCTP | ND | ND | <2.6 | <2.6 |
| Preimmunization | <2.6 | <2.6 | <2.6 | <2.6 |

*$\log_{10}$ mean ± SE IgG isotype specific antibody titer
ND = not done

REFERENCES

1. M. A. Liu, M. R. Hilleman, R. Kurth, Ann. N.Y. Acad. Sci. 772 (1995).
2. D. M. Pardoll and A. M. Beckerieg, Immunity 3, 165 (1995); W. M. McDonnell and F. K. Askari, N. Engl. J. Med. 334, 42 (1996).
3. J. B. Ulmer et al., Science 259, 1745 (1993); B. Wang et al., Proc. Natl. Acad. Sci. USA 90, 4156 (1993); G. J. M. Cox, T. J. Zamb, L. A. Babiuk, J. Virol. 67, 5664 (1993); E. Raz et al., Proc. Natl. Acad. Sci. USA, 91,9519 (1994); Z. Q. Xiang et al., Virology 199, 132 (1994); J. J. Donnelly et al., J. Infect. Dis. 713, 314 (1996); D. L. Montgomery et al., DNA. Cell. Biol. 12, 777 (1993); J. J. Donnelly et al., Nature Medicine 1, 583 (1995); G. H. Rhodes et al., Dev. Biol. Stand. 82, 229 (1994); H. L. Davis, M. L. Michel, R. G. Whalen, Human Molecular Genetics 2, 1847 (1993); J. B. Ulmer et al., Vaccine 12, 1541 (1994); Z. Xiang and H. C. J. Ertl. Immunity 2, 129 (1995); E. F. Fynan et al, Proc. Natl. Acad. Sci. USA 90, 11478 (1993); E. Manickan, R. J. D. Rouse, Z. Yu, J. Immunol. 155, 259 (1995).
4. M. Sedegah, R. Hedstrom, P. Hobart, S. L. Hoffman, Proc. Natl. Acad. Sci. USA 91, 9866 (1994); M. A. Barry, W. C. Lai, S. A. Johnston, Nature 377, 632 (1995); D. Xu and F. Y. Liew, Vaccine 12, 1534 (1994); D. B. Lowrie, R. E. Tascon, M. J. Colston, Vaccine 12, 1537 (1994).
5. J. W. Moulder, Microbiol. Rev. 55, 143 (1991).
6. J. Schachter, Curr. Top. Microbiol. Immunol. 138, 109 (1988); S. D. Hillis and J. N. Wasserheit, N. Engl. J. Med. 334, 1399 (1996).
7. R. C. Brunham and R. W. Peeling, Infectious Agents and Disease 3, 218 (1994); R. P. Morrison, D. S. Manning, H. D. Caldwell, in Advances in Host Defence Mechanisms, T. C. Quin, Ed. (Raven Press, New York, 1992), pp 57–84.
8. J. T. Grayston and S.-P. Wang, Sex. Trans. Dis. 5, 73 (1978); J. T. Grayston and S.-P. Wang, J. Infect. Dis. 132, 87 (1975).
9. H. R. Taylor, J. Whittum-Hudson, J. Schachter, Invest. Ophthalmol. Vis. Sci. 29, 1847 (1988); B. E. Batteiger, R. G. Rank, P. M. Bavoil, J. Gen. Microbiol. 139, 2965 (1993); M. Campos et al., Invest. Ophthalmol. Vis. Sci. 36, 1477 (1995); H. Su, M. Parnell, H. D. Caldwell, Vaccine 13, 1023 (1995); T.-W. Tan, A. J. Herring, I. E. Anderson, Infect. Immun. 58, 3101 (1990); M. Tuffrey, F. Alexander, W. Conlan, J. Gen. Microbiol. 138, 1707 (1992).
10. Y.-X. Zhang, J. G. Fox, Y. Ho, Mol. Biol. Evol. 10, 1327 (1993).
11. R. P. Morrison, K. Feilzer, D. B. Tumas, Infect. Immun. 63, 4661 (1995); H. Su and H. D. Caldwell, Infect. Immun. 63, 3302 (1995); J. U. Igietseme et al., Reg. Immunol. 5, 317 (1993); J. U. Igietseme and R. G. Rank, Infect. Immun. 59, 1346 (1991); D. M. Williams, J. Schachter, J. J. Coalson, J. Infect. Dis. 149, 630 (1984).
12. G. Tipples and G. McClarty, J. Biol. Chem. 270, 7908 (1995).
13. X. Yang, K. T. HayGlass, R. C. Brunham, J. Immunol., 156, 4338 (1996).
14. H. Su and H. D. Caldwell, Infect. Immun. 63, 946 (1995).
15. A. S. McWilliam, D. Nelson, J. A. Thomas, J. Exp. Med. 179, 1331 (1994); M. R. Neutra, E. Pringault, J.-P. Kraehenbuhl, Annu. Rev. Immunol. 14, 275 (1996); J. M. Austyn, J. Exp. Med. 183, 1287 (1996).
16. R. Brunham et al., J. Clin. Invest. 94, 458 (1994); R. C. Brunham et al., J. Infect. Dis. 173, 950 (1996).
17. Tang et al., Nature 1992, 356:152–154.
18. Davis et al., Vaccine 1994, 12:1503:1509.
19. Morrison RP, Manning DS, Caldwell HD. Immunology of *Chlamydia trachomatis* infections: Immunoprotective and immunopathogenetic responses. In: Quin TC. Advances in host defence mechanisms. Sexually transmitted diseases. Vol. 8. New York: Raven Press, 1992: 52–84.
20. Brunham R., Yang C., Maclean I., Kimani J., Maitha G., Plummer F., *Chlamydia trachomatis* from individuals in a sexually transmitted disease core group exhibit frequent sequence variation in the major outer membrane protein (ompl) gene. J. Clin. Invest. 1994; 94:458–63.
21. Xiang Z. Ertl HCJ. Manipulation of the immune response to a plasmid-encoded viral antigen by coinoculation with plasmids expressing cytokines. Immunity 1995:2:129–35.
22. Holland M. J. et al, Synthetic peptides based on *Chlamydia trachomatis* antigens identify cytotoxic T lymphocyte responses in subjects from a trachoma-endemic population. Clin. Exp. Immunol. 1997 January; 107(1):44–49.
23. Su H. et al., Identification and characterization of T helper cell epitopes of the major outer membrane protein of *Chlamydia trachomatis*. J. Exp. Med. 1990 Jul. 1:172 (1):203–212.
24. Su H. et al, Immunogenicity of a chimeric peptide corresponding to T helper and B cell epitopes of the *Chlamydia trachomatis* major outer membrane protein. J. Exp. Med. 1992, Jan. 1; 175(1): 227–235.
25. Allen J. E. et al., A single peptide from the major outer membrane protein of *Chlamydia trachomatis* elicits T cell help for the production of antibodies to protective determinants. J. Immunol. 1991, Jul. 15;147(2):674–679.
26. Knight S. C. et al, A peptide of *Chlamydia trachomatis* shown to be a primary T-cell epitope in vitro induces cell-mediated immunity in vivo. PMID: 1712817, UI:91302820.

I claim:

1. A method of immunizing a host against disease caused by infection with a strain of *Chlamydia*, which comprises administering to said host an effective amount of a non-replicating vector comprising:
   a nucleotide sequence encoding a region consisting of at least one of the conserved domains 2, 3 and 5 of a major outer membrane protein (MOMP) of a strain of *Chlamydia*, and
   a promoter sequence operatively coupled to said nucleotide sequence for expression of said at least one conserved domain in the host.

2. The method of claim 1 wherein said promoter sequence is the cytomegalovirus promoter.

3. The method of claim 1 wherein said strain of *Chlamydia* is a strain producing chlamydial infections of the lung.

4. The method of claim 1 wherein said strain of *Chlamydia* is a strain of *Chlamydia trachomatis*.

5. The method of claim 1 wherein said non-replicating vector comprises plasmid pcDNA3 containing said promoter into which said nucleotide sequence is inserted in operative relation to said promoter sequence.

6. The method of claim 1 wherein said immune response is predominantly a cellular immune response.

7. The method of claim 1 wherein said non-replicating vector is administered intranasally.

8. The method of claim 1 wherein said host is a human host.

9. A method of using a nucleotide sequence encoding a fragment of a major outer membrane protein (MOMP) of a strain of *Chiamydia* that generates a MOMP-specific immune response, to produce an immune response in a host, which comprises:
   isolating said nucleotide sequence encoding a region consisting of at least one of the conserved domains 2, 3 and 5 of a major outer membrane protein of a strain of *Chlamydia*,
   operatively linking said nucleotide sequence to at least one control sequence to produce a non-replicating vector, said control sequence directing expression of said MOMP fragment when introduced into a host to produce an immune response to said MOMP fragment, and
   introducing said vector into a host.

10. A method of using a nucleotide sequence encoding a fragment of a major outer membrane protein (MOMP) of a strain of *Chlamydia* that generates a MOMP-specific immune response, to produce an immune response in a host, which comprises:
   isolating a nucleotide sequence encoding a region consisting of at least one of the conserved domains 2 and 3 of the MOMP of a strain of Chiamydia and further consisting of a nucleotide sequence encoding a variable domain of the major outer membrane protein immediately downstream of said conserved domain,
   operatively linking said nucleotide sequence to at least one control sequence to produce a non-replicating vector, said control sequence directing expression of said MOMP fragment when introduced into a host to produce an immune response to said MOMP fragment, and
   introducing said vector into a host.

11. The method of claim 9 wherein said nucleotide sequence encodes the conserved domain 5 of a major outer membrane protein of a strain of *Chlamydia*.

12. The method of claim 9 wherein said control sequence is the cytomegalovirus promoter.

13. The method of claim 9 wherein said strain of *Chlamydia* is a strain producing chiamydial infections of the lung.

14. The method of claim 9 wherein said strain of *Chlamydia* is a strain of *Chlamydia trachomatis*.

15. The method of claim 9 wherein said non-replicating vector comprises plasmid pcDNA3 containing said control sequence into which said gene encoding MOMP is inserted in operative relation to said control sequence.

16. The method of claim 9 wherein said immune response is predominantly a cellular immune response.

17. The method of claim 9 wherein said vector is introduced into said host intranasally.

18. The method of claim 9 wherein said host is a human host.

19. A method of immunizing a host against disease caused by infection with a strain of *Chlamydia*, which comprises administering to said host an effective amount of a non-replicating vector comprising:
   a nucleotide sequence encoding a region consisting of at least one of the conserved domains 2 and 3 of a major outer membrane protein (MOM P) of a strain of *Chlamydia* and further consisting of a nucleotide sequence encoding a variable domain of the major outer membrane protein immediately downstream of said conserved domain, and
   a promoter sequence operatively coupled to said nucleotide sequence for expression of said at least one conserved domain and variable domain in the host.

20. The method of claim 19 wherein said promoter sequence is the cytomegalovirus promoter.

21. The method of claim 19 wherein said strain of *Chlamydia* is a strain producing chlamydial infections of the lung.

22. The method of claims 19 wherein said strain of *Chlamydia* is a strain of *Chiamydia trachomatis*.

23. The method of claim 19 wherein said non-replicating vector comprises plasmid pcDNA3 containing said promoter into which said nucleotide sequence is inserted in operative relation to said promoter sequence.

24. The method of claim 19 wherein said immune response is predominantly a cellular immune response.

25. The method of claims 19 wherein said non-replicating vector is administered intranasally.

* * * * *

SEQUENCE LISTING

<160> NUMBER OF SEQ ID NOS: 17

<210> SEQ ID NO 1
<211> LENGTH: 393
<212> TYPE: PRT
<213> ORGANISM: Chlamydia trachomatis

<400> SEQUENCE: 1

```
Met Lys Lys Leu Leu Lys Ser Val Leu Val Phe Ala Ala Leu Ser Ser
 1               5                  10                  15

Ala Ser Ser Leu Gln Ala Leu Pro Val Gly Asn Pro Ala Glu Pro Ser
                20                  25                  30

Leu Met Ile Asp Gly Ile Leu Trp Glu Gly Phe Gly Gly Asp Pro Cys
            35                  40                  45

Asp Pro Cys Thr Thr Trp Cys Asp Ala Ile Ser Met Arg Met Gly Tyr
        50                  55                  60

Tyr Gly Asp Phe Val Phe Asp Arg Val Leu Lys Thr Asp Val Asn Lys
 65                  70                  75                  80

Glu Phe Gln Met Gly Asp Lys Pro Thr Ser Thr Thr Gly Asn Ala Thr
                85                  90                  95

Ala Pro Thr Thr Leu Thr Ala Arg Glu Asn Pro Ala Tyr Gly Arg His
            100                 105                 110

Met Gln Asp Ala Glu Met Phe Thr Asn Ala Ala Cys Met Ala Leu Asn
        115                 120                 125

Ile Trp Asp Arg Phe Asp Val Phe Cys Thr Leu Gly Ala Ser Ser Gly
    130                 135                 140

Tyr Leu Lys Gly Asn Ser Ala Ser Phe Asn Leu Val Gly Leu Phe Gly
145                 150                 155                 160

Asp Asn Glu Asn Gln Ser Thr Val Lys Thr Asn Ser Val Pro Asn Met
                165                 170                 175

Ser Leu Asp Gln Ser Val Val Glu Leu Tyr Thr Asp Thr Ala Phe Ser
            180                 185                 190

Trp Ser Val Gly Ala Arg Ala Ala Leu Trp Glu Cys Gly Cys Ala Thr
        195                 200                 205

Leu Gly Ala Ser Phe Gln Tyr Ala Gln Ser Lys Pro Lys Val Glu Glu
    210                 215                 220

Leu Asn Val Leu Cys Asn Ala Ala Glu Phe Thr Ile Asn Lys Pro Lys
225                 230                 235                 240

Gly Tyr Val Gly Gln Glu Phe Pro Leu Ala Leu Ile Ala Gly Thr Asp
                245                 250                 255

Ala Ala Thr Gly Thr Lys Asp Ala Ser Ile Asp Tyr Asn Glu Trp Gln
            260                 265                 270

Ala Ser Leu Ala Leu Ser Tyr Arg Leu Asn Met Phe Thr Pro Tyr Ile
        275                 280                 285

Gly Val Lys Trp Ser Arg Ala Ser Phe Asp Ala Asp Thr Ile Arg Ile
    290                 295                 300

Ala Gln Pro Lys Ser Ala Thr Ala Ile Phe Asp Thr Thr Leu Asn
305                 310                 315                 320

Pro Thr Ile Ala Gly Ala Gly Asp Val Lys Ala Ser Ala Glu Gly Gln
                325                 330                 335

Leu Gly Asp Thr Met Gln Ile Val Ser Leu Gln Leu Asn Lys Met Lys
            340                 345                 350

Ser Arg Lys Ser Cys Gly Ile Ala Val Gly Thr Thr Ile Val Asp Ala
```

```
                     355                 360                 365
Asp Lys Tyr Ala Val Thr Val Glu Thr Arg Leu Ile Asp Glu Arg Ala
        370                 375                 380

Ala His Val Asn Ala Gln Phe Arg Phe
385                 390

<210> SEQ ID NO 2
<211> LENGTH: 394
<212> TYPE: PRT
<213> ORGANISM: Chlamydia trachomatis

<400> SEQUENCE: 2

Met Lys Lys Leu Leu Lys Ser Val Leu Val Phe Ala Ala Leu Ser Ser
  1               5                  10                  15

Ala Ser Ser Leu Gln Ala Leu Pro Val Gly Asn Pro Ala Glu Pro Ser
                 20                  25                  30

Leu Met Ile Asp Gly Ile Leu Trp Glu Gly Phe Gly Gly Asp Pro Cys
             35                  40                  45

Asp Pro Cys Thr Thr Trp Cys Asp Ala Ile Ser Met Arg Met Gly Tyr
         50                  55                  60

Tyr Gly Asp Phe Val Phe Asp Arg Val Leu Lys Thr Asp Val Asn Lys
 65                  70                  75                  80

Glu Phe Gln Met Gly Ala Lys Pro Thr Thr Thr Gly Asn Ala Val
                 85                  90                  95

Ala Pro Ser Thr Leu Thr Ala Arg Glu Asn Pro Ala Tyr Gly Arg His
                100                 105                 110

Met Gln Asp Ala Glu Met Phe Thr Asn Ala Ala Cys Met Ala Leu Asn
            115                 120                 125

Ile Trp Asp Arg Phe Asp Val Phe Cys Thr Leu Gly Ala Ser Ser Gly
130                 135                 140

Tyr Leu Lys Gly Asn Ser Ala Ser Phe Asn Leu Val Gly Leu Phe Gly
145                 150                 155                 160

Asn Asn Glu Asn Gln Thr Lys Val Ser Asn Gly Ala Phe Val Pro Asn
                165                 170                 175

Met Ser Leu Asp Gln Ser Val Val Glu Leu Tyr Thr Asp Thr Ala Phe
            180                 185                 190

Ala Trp Ser Val Gly Ala Arg Ala Ala Leu Trp Glu Cys Gly Cys Ala
        195                 200                 205

Thr Leu Gly Ala Ser Phe Gln Tyr Ala Gln Ser Lys Pro Lys Val Glu
    210                 215                 220

Glu Leu Asn Val Leu Cys Asn Ala Ala Glu Phe Thr Ile Asn Lys Pro
225                 230                 235                 240

Lys Gly Tyr Val Gly Lys Glu Leu Pro Leu Asp Leu Thr Ala Gly Thr
                245                 250                 255

Asp Ala Ala Thr Gly Thr Lys Asp Ala Ser Ile Asp Tyr Asn Glu Trp
            260                 265                 270

Gln Ala Ser Leu Ala Leu Ser Tyr Arg Leu Asn Met Phe Thr Pro Tyr
        275                 280                 285

Ile Gly Val Lys Trp Ser Arg Ala Ser Phe Asp Ala Asp Thr Ile Arg
    290                 295                 300

Ile Ala Gln Pro Lys Ser Ala Glu Thr Ile Phe Asp Val Thr Thr Leu
305                 310                 315                 320

Asn Pro Thr Ile Ala Gly Ala Gly Asp Val Lys Thr Ser Ala Glu Gly
                325                 330                 335
```

```
Gln Leu Gly Asp Thr Met Gln Ile Val Ser Leu Gln Leu Asn Lys Met
            340                 345                 350

Lys Ser Arg Lys Ser Cys Gly Ile Ala Val Gly Thr Thr Ile Val Asp
            355                 360                 365

Ala Asp Lys Tyr Ala Val Thr Val Glu Thr Arg Leu Ile Asp Glu Arg
            370                 375                 380

Ala Ala His Val Asn Ala Gln Phe Arg Phe
385                 390
```

<210> SEQ ID NO 3
<211> LENGTH: 393
<212> TYPE: PRT
<213> ORGANISM: Chlamydia trachomatis

<400> SEQUENCE: 3

```
Met Lys Lys Leu Leu Lys Ser Val Leu Val Phe Ala Ala Leu Ser Ser
  1               5                  10                  15

Ala Ser Ser Leu Gln Ala Leu Pro Val Gly Asn Pro Ala Glu Pro Ser
             20                  25                  30

Leu Met Ile Asp Gly Ile Leu Trp Glu Gly Phe Gly Gly Asp Pro Cys
         35                  40                  45

Asp Pro Cys Thr Thr Trp Cys Asp Ala Ile Ser Met Arg Met Gly Tyr
     50                  55                  60

Tyr Gly Asp Phe Val Phe Asp Arg Val Leu Gln Thr Asp Val Asn Lys
 65                  70                  75                  80

Glu Phe Gln Met Gly Ala Lys Pro Thr Ala Thr Gly Asn Ala Ala
                 85                  90                  95

Ala Pro Ser Thr Cys Thr Ala Arg Glu Asn Pro Ala Tyr Gly Arg His
            100                 105                 110

Met Gln Asp Ala Glu Met Phe Thr Asn Ala Ala Tyr Met Ala Leu Asn
            115                 120                 125

Ile Trp Asp Arg Phe Asp Val Phe Cys Thr Leu Gly Ala Thr Ser Gly
130                 135                 140

Tyr Leu Lys Gly Asn Ser Ala Ser Phe Asn Leu Val Gly Leu Phe Gly
145                 150                 155                 160

Asp Asn Glu Asn Gln Ser Thr Val Lys Lys Asp Ala Val Pro Asn Met
                165                 170                 175

Ser Phe Asp Gln Ser Val Val Glu Leu Tyr Thr Asp Thr Thr Phe Ala
            180                 185                 190

Trp Ser Val Gly Ala Arg Ala Ala Leu Trp Glu Cys Gly Cys Ala Thr
            195                 200                 205

Leu Gly Ala Ser Phe Gln Tyr Ala Gln Ser Lys Pro Lys Val Glu Glu
            210                 215                 220

Leu Asn Val Leu Cys Asn Ala Ala Glu Phe Thr Ile Asn Lys Pro Lys
225                 230                 235                 240

Gly Tyr Val Gly Lys Glu Phe Pro Leu Asp Leu Thr Ala Gly Thr Asp
                245                 250                 255

Ala Ala Thr Gly Thr Lys Asp Ala Ser Ile Asp Tyr Asn Glu Trp Gln
            260                 265                 270

Ala Ser Leu Ala Leu Ser Tyr Arg Leu Asn Met Phe Thr Pro Tyr Ile
            275                 280                 285

Gly Val Lys Trp Ser Arg Ala Ser Phe Asp Ala Asp Thr Ile Arg Ile
        290                 295                 300

Ala Gln Pro Lys Leu Ala Thr Ala Ile Phe Asp Thr Thr Thr Leu Asn
305                 310                 315                 320
```

-continued

```
Pro Thr Ile Ala Gly Ala Gly Glu Val Lys Ala Asn Ala Glu Gly Gln
            325                 330                 335

Leu Gly Asp Thr Met Gln Ile Val Ser Leu Gln Leu Asn Lys Met Lys
            340                 345                 350

Ser Arg Lys Ser Cys Gly Ile Ala Val Gly Thr Thr Ile Val Asp Ala
            355                 360                 365

Asp Lys Tyr Ala Val Thr Val Glu Thr Arg Leu Ile Asp Glu Arg Ala
    370                 375                 380

Ala His Val Asn Ala Gln Phe Arg Phe
385                 390
```

<210> SEQ ID NO 4
<211> LENGTH: 393
<212> TYPE: PRT
<213> ORGANISM: Chlamydia trachomatis

<400> SEQUENCE: 4

```
Met Lys Lys Leu Leu Lys Ser Val Leu Val Phe Ala Ala Leu Ser Ser
  1               5                  10                  15

Ala Ser Ser Leu Gln Ala Leu Pro Val Gly Asn Pro Ala Glu Pro Ser
            20                  25                  30

Leu Met Ile Asp Gly Ile Leu Trp Glu Gly Phe Gly Gly Asp Pro Cys
        35                  40                  45

Asp Pro Cys Thr Thr Trp Cys Asp Ala Ile Ser Met Arg Met Gly Tyr
    50                  55                  60

Tyr Gly Asp Phe Val Phe Asp Arg Val Leu Glu Thr Asp Val Asn Lys
65                  70                  75                  80

Glu Phe His Met Gly Ala Lys Pro Thr Ser Thr Thr Gly Asn Ala Thr
                85                  90                  95

Ala Pro Thr Thr Leu Thr Ala Arg Glu Asn Pro Ala Tyr Gly Arg His
            100                 105                 110

Met Gln Asp Ala Glu Met Phe Thr Asn Ala Ala Cys Met Ala Leu Asn
        115                 120                 125

Ile Trp Asp Arg Phe Asp Val Phe Cys Thr Leu Gly Ala Thr Ser Gly
    130                 135                 140

Tyr Leu Lys Gly Asn Ser Ala Ser Phe Asn Leu Val Gly Leu Phe Gly
145                 150                 155                 160

Asp Asn Glu Asn Gln Lys Thr Val Lys Ala Glu Ser Val Pro Asn Met
                165                 170                 175

Ser Phe Asp Gln Ser Val Val Glu Leu Tyr Thr Asp Thr Phe Ala
        180                 185                 190

Trp Ser Val Gly Ala Arg Ala Ala Leu Trp Glu Cys Gly Cys Ala Thr
    195                 200                 205

Leu Gly Ala Ser Phe Gln Tyr Ala Gln Ser Lys Pro Lys Val Glu Glu
    210                 215                 220

Leu Asn Val Leu Cys Asn Ala Ala Glu Phe Thr Ile Asn Lys Pro Lys
225                 230                 235                 240

Gly Tyr Val Gly Lys Glu Phe Pro Leu Asp Leu Thr Ala Gly Thr Asp
                245                 250                 255

Ala Ala Thr Gly Thr Lys Asp Ala Ser Ile Asp Tyr Asn Glu Trp Gln
            260                 265                 270

Ala Ser Leu Ala Leu Ser Tyr Arg Leu Asn Met Phe Thr Pro Tyr Ile
        275                 280                 285

Gly Val Lys Trp Ser Arg Ala Ser Phe Asp Ala Asp Thr Ile Arg Ile
```

```
                290                 295                 300
Ala Gln Pro Lys Ser Ala Thr Ala Ile Phe Asp Thr Thr Thr Leu Asn
305                 310                 315                 320

Pro Thr Ile Ala Gly Ala Gly Asp Val Lys Thr Gly Thr Glu Gly Gln
                325                 330                 335

Leu Gly Asp Thr Met Gln Ile Val Ser Leu Gln Leu Asn Lys Met Lys
                340                 345                 350

Ser Arg Lys Ser Cys Gly Ile Ala Val Gly Thr Thr Ile Val Asp Ala
                355                 360                 365

Asp Lys Tyr Ala Val Thr Val Glu Thr Arg Leu Ile Asp Glu Arg Ala
370                 375                 380

Ala His Val Asn Ala Gln Phe Arg Phe
385                 390

<210> SEQ ID NO 5
<211> LENGTH: 394
<212> TYPE: PRT
<213> ORGANISM: Chlamydia trachomatis

<400> SEQUENCE: 5

Met Lys Lys Leu Leu Lys Ser Val Leu Val Phe Ala Ala Leu Ser Ser
  1               5                  10                  15

Ala Ser Ser Leu Gln Ala Leu Pro Val Gly Asn Pro Ala Glu Pro Ser
                 20                  25                  30

Leu Met Ile Asp Gly Ile Leu Trp Glu Gly Phe Gly Gly Asp Pro Cys
             35                  40                  45

Asp Pro Cys Thr Thr Trp Cys Asp Ala Ile Ser Met Arg Met Gly Tyr
         50                  55                  60

Tyr Gly Asp Phe Val Phe Asp Arg Val Leu Gln Thr Asp Val Asn Lys
 65                  70                  75                  80

Glu Phe Gln Met Gly Ala Lys Pro Thr Thr Ala Thr Gly Asn Ala Ala
                 85                  90                  95

Ala Pro Ser Thr Cys Thr Ala Arg Glu Asn Pro Ala Tyr Gly Arg His
                100                 105                 110

Met Gln Asp Ala Glu Met Phe Thr Asn Ala Ala Tyr Met Ala Leu Asn
            115                 120                 125

Ile Trp Asp Arg Phe Asp Val Phe Cys Thr Leu Gly Ala Thr Ser Gly
        130                 135                 140

Tyr Leu Lys Gly Asn Ser Ala Ser Phe Asn Leu Val Gly Leu Phe Gly
145                 150                 155                 160

Asp Asn Glu Asn His Ala Thr Val Ser Asp Ser Lys Leu Val Pro Asn
                165                 170                 175

Met Ser Leu Asp Gln Ser Val Val Glu Leu Tyr Thr Asp Thr Thr Phe
            180                 185                 190

Ala Trp Ser Ala Gly Ala Arg Ala Ala Leu Trp Glu Cys Gly Cys Ala
        195                 200                 205

Thr Leu Gly Ala Ser Phe Gln Tyr Ala Gln Ser Lys Pro Lys Val Glu
    210                 215                 220

Glu Leu Asn Val Leu Cys Asn Ala Ala Glu Phe Thr Ile Asn Lys Pro
225                 230                 235                 240

Lys Gly Tyr Val Gly Gln Glu Phe Pro Leu Asp Leu Lys Ala Gly Thr
                245                 250                 255

Asp Gly Val Thr Gly Thr Lys Asp Ala Ser Ile Asp Tyr Asn Glu Trp
            260                 265                 270
```

```
Gln Ala Ser Leu Ala Leu Ser Tyr Arg Leu Asn Met Phe Thr Pro Tyr
        275                 280                 285

Ile Gly Val Lys Trp Ser Arg Ala Ser Phe Asp Ala Asp Thr Ile Arg
        290                 295                 300

Ile Ala Gln Pro Lys Ser Ala Thr Thr Val Phe Asp Val Thr Thr Leu
305                 310                 315                 320

Asn Pro Thr Ile Ala Gly Ala Asp Val Lys Ala Ser Ala Glu Gly
                325                 330                 335

Gln Leu Gly Asp Thr Met Gln Ile Val Ser Leu Gln Leu Asn Lys Met
            340                 345                 350

Lys Ser Arg Lys Ser Cys Gly Ile Ala Val Gly Thr Thr Ile Val Asp
            355                 360                 365

Ala Asp Lys Tyr Ala Val Thr Val Glu Thr Arg Leu Ile Asp Glu Arg
370                 375                 380

Ala Ala His Val Asn Ala Gln Phe Arg Phe
385                 390

<210> SEQ ID NO 6
<211> LENGTH: 395
<212> TYPE: PRT
<213> ORGANISM: Chlamydia trachomatis

<400> SEQUENCE: 6

Met Lys Lys Leu Leu Lys Ser Val Leu Val Phe Ala Ala Leu Ser Ser
 1               5                  10                  15

Ala Ser Ser Leu Gln Ala Leu Pro Val Gly Asn Pro Ala Glu Pro Ser
            20                  25                  30

Leu Met Ile Asp Gly Ile Leu Trp Glu Gly Phe Gly Gly Asp Pro Cys
        35                  40                  45

Asp Pro Cys Thr Thr Trp Cys Asp Ala Ile Ser Met Arg Met Gly Tyr
    50                  55                  60

Tyr Gly Asp Phe Val Phe Asp Arg Val Leu Lys Thr Asp Val Asn Lys
65                  70                  75                  80

Glu Phe Glu Met Gly Glu Ala Leu Ala Gly Ala Ser Gly Asn Thr Thr
                85                  90                  95

Ser Thr Leu Ser Lys Leu Val Glu Arg Thr Asn Pro Ala Tyr Gly Lys
            100                 105                 110

His Met Gln Asp Ala Glu Met Phe Thr Asn Ala Ala Cys Met Thr Leu
        115                 120                 125

Asn Ile Trp Asp Arg Phe Asp Val Phe Cys Thr Leu Gly Ala Thr Ser
    130                 135                 140

Gly Tyr Leu Lys Gly Asn Ser Ala Ser Phe Asn Leu Val Gly Leu Phe
145                 150                 155                 160

Gly Asp Gly Val Asn Ala Thr Lys Pro Ala Ala Asp Ser Ile Pro Asn
                165                 170                 175

Val Gln Leu Asn Gln Ser Val Val Glu Leu Tyr Thr Asp Thr Thr Phe
            180                 185                 190

Ala Trp Ser Val Gly Ala Arg Ala Ala Leu Trp Glu Cys Gly Cys Ala
        195                 200                 205

Thr Leu Gly Ala Ser Phe Gln Tyr Ala Gln Ser Lys Pro Lys Ile Glu
    210                 215                 220

Glu Leu Asn Val Leu Cys Asn Ala Ala Glu Phe Thr Ile Asn Lys Pro
225                 230                 235                 240

Lys Gly Tyr Val Gly Lys Glu Phe Pro Leu Asp Leu Thr Ala Gly Thr
                245                 250                 255
```

-continued

Asp Ala Ala Thr Gly Thr Lys Asp Ala Ser Ile Asp Tyr Asn Glu Trp
                260                 265                 270

Gln Ala Ser Leu Ser Leu Ser Tyr Arg Leu Asn Met Phe Thr Pro Tyr
            275                 280                 285

Ile Gly Val Lys Trp Ser Arg Ala Ser Phe Asp Ser Asp Thr Ile Arg
        290                 295                 300

Ile Ala Gln Pro Arg Leu Val Thr Pro Val Asp Ile Thr Leu
305                 310                 315                 320

Asn Pro Thr Ile Ala Gly Cys Gly Ser Val Ala Gly Ala Asn Thr Glu
                325                 330                 335

Gly Gln Ile Ser Asp Thr Met Gln Ile Val Ser Leu Gln Leu Asn Lys
            340                 345                 350

Met Lys Ser Arg Lys Ser Cys Gly Ile Ala Val Gly Thr Thr Ile Val
        355                 360                 365

Asp Ala Asp Lys Tyr Ala Val Thr Val Glu Thr Arg Leu Ile Asp Glu
    370                 375                 380

Arg Ala Ala His Val Asn Ala Gln Phe Arg Phe
385                 390                 395

<210> SEQ ID NO 7
<211> LENGTH: 397
<212> TYPE: PRT
<213> ORGANISM: Chlamydia trachomatis

<400> SEQUENCE: 7

Met Lys Lys Leu Leu Lys Ser Val Leu Val Phe Ala Ala Leu Ser Ser
  1               5                  10                  15

Ala Ser Ser Leu Gln Ala Leu Pro Val Gly Asn Pro Ala Glu Pro Ser
                20                  25                  30

Leu Met Ile Asp Gly Ile Leu Trp Glu Gly Phe Gly Gly Asp Pro Cys
            35                  40                  45

Asp Pro Cys Thr Thr Trp Cys Asp Ala Ile Ser Met Arg Val Gly Tyr
        50                  55                  60

Tyr Gly Asp Phe Val Phe Asp Arg Val Leu Lys Thr Asp Val Asn Lys
 65                  70                  75                  80

Glu Phe Gln Met Gly Ala Glu Pro Thr Thr Ser Asp Thr Ala Gly Leu
                85                  90                  95

Ser Asn Asp Pro Thr Thr Asn Val Ala Arg Pro Asn Pro Ala Tyr Gly
               100                 105                 110

Lys His Met Gln Asp Ala Glu Met Phe Thr Asn Ala Ala Tyr Met Ala
           115                 120                 125

Leu Asn Ile Trp Asp Arg Phe Asp Val Phe Cys Thr Leu Gly Ala Thr
       130                 135                 140

Thr Gly Tyr Leu Lys Gly Asn Ser Ala Ser Phe Asn Leu Val Gly Leu
145                 150                 155                 160

Phe Gly Thr Lys Thr Gln Ser Thr Asn Phe Asn Thr Ala Lys Leu Val
                165                 170                 175

Pro Asn Thr Ala Leu Asn Gln Ala Val Val Glu Leu Tyr Thr Asp Thr
            180                 185                 190

Thr Phe Ala Trp Ser Val Gly Ala Arg Ala Ala Leu Trp Glu Cys Gly
        195                 200                 205

Cys Ala Thr Leu Gly Ala Ser Phe Gln Tyr Ala Gln Ser Lys Pro Lys
    210                 215                 220

Val Glu Glu Leu Asn Val Leu Cys Asp Ala Ser Glu Phe Thr Ile Asn

```
            225                 230                 235                 240
Lys Pro Lys Gly Tyr Val Gly Ala Glu Phe Pro Leu Asp Ile Thr Ala
                245                 250                 255

Gly Thr Glu Ala Ala Thr Gly Thr Lys Asp Ala Ser Ile Asp Tyr Asn
            260                 265                 270

Glu Trp Gln Ala Ser Leu Ala Leu Ser Tyr Arg Leu Asn Met Phe Thr
        275                 280                 285

Pro Tyr Ile Gly Val Lys Trp Ser Arg Val Ser Phe Asp Ala Asp Thr
    290                 295                 300

Ile Arg Ile Ala Gln Pro Lys Leu Ala Glu Ala Val Leu Asp Val Thr
305                 310                 315                 320

Thr Leu Asn Pro Thr Ile Ala Gly Lys Gly Ser Val Val Ala Ser Gly
                325                 330                 335

Ser Glu Asn Glu Leu Ala Asp Thr Met Gln Ile Val Ser Leu Gln Leu
            340                 345                 350

Asn Lys Met Lys Ser Arg Lys Ser Cys Gly Ile Ala Val Gly Thr Thr
        355                 360                 365

Ile Val Asp Ala Asp Lys Tyr Ala Val Thr Val Glu Thr Arg Leu Ile
    370                 375                 380

Asp Glu Arg Ala Ala His Val Asn Ala Gln Phe Arg Phe
385                 390                 395
```

<210> SEQ ID NO 8
<211> LENGTH: 396
<212> TYPE: PRT
<213> ORGANISM: Chlamydia trachomatis

<400> SEQUENCE: 8

```
Met Lys Lys Leu Leu Lys Ser Val Leu Val Phe Ala Ala Leu Ser Ser
  1               5                  10                  15

Ala Ser Ser Leu Gln Ala Leu Pro Val Gly Asn Pro Ala Glu Pro Ser
            20                  25                  30

Leu Met Ile Asp Gly Ile Leu Trp Glu Gly Phe Gly Gly Asp Pro Cys
        35                  40                  45

Asp Pro Cys Thr Thr Trp Cys Asp Ala Ile Ser Met Arg Met Gly Tyr
    50                  55                  60

Tyr Gly Asp Phe Val Phe Asp Arg Val Leu Lys Thr Asp Val Asn Lys
65                  70                  75                  80

Glu Phe Gln Met Gly Ala Ala Pro Thr Thr Ser Asp Val Ala Gly Leu
                85                  90                  95

Glu Lys Asp Pro Val Ala Asn Val Ala Arg Pro Asn Pro Ala Tyr Gly
            100                 105                 110

Lys His Met Gln Asp Ala Glu Met Phe Thr Asn Ala Ala Tyr Met Ala
        115                 120                 125

Leu Asn Ile Trp Asp Arg Phe Asp Val Phe Cys Thr Leu Gly Ala Thr
    130                 135                 140

Thr Gly Tyr Leu Lys Gly Asn Ser Ala Ser Phe Asn Leu Val Gly Leu
145                 150                 155                 160

Phe Gly Thr Lys Thr Gln Ser Ser Gly Phe Asp Thr Ala Asn Ile Val
                165                 170                 175

Pro Asn Thr Ala Leu Asn Gln Ala Val Val Glu Leu Tyr Thr Asp Thr
            180                 185                 190

Thr Phe Ala Trp Ser Val Gly Ala Arg Ala Ala Leu Trp Glu Cys Gly
        195                 200                 205
```

-continued

```
Cys Ala Thr Leu Gly Ala Ser Phe Gln Tyr Ala Gln Ser Lys Pro Lys
    210                 215                 220

Val Glu Glu Leu Asn Val Leu Cys Asn Ala Ser Glu Phe Thr Ile Asn
225                 230                 235                 240

Lys Pro Lys Gly Tyr Val Gly Ala Glu Phe Pro Leu Asp Ile Thr Ala
                245                 250                 255

Gly Thr Glu Ala Ala Thr Gly Thr Lys Asp Ala Ser Ile Asp Tyr Asn
                260                 265                 270

Glu Trp Gln Ala Ser Leu Ala Leu Ser Tyr Arg Leu Asn Met Phe Thr
            275                 280                 285

Pro Tyr Ile Gly Val Lys Trp Ser Arg Val Ser Phe Asp Ala Asp Thr
    290                 295                 300

Ile Arg Ile Ala Gln Pro Lys Leu Ala Lys Pro Val Leu Asp Thr Thr
305                 310                 315                 320

Thr Leu Asn Pro Thr Ile Ala Gly Lys Gly Thr Val Val Ser Ser Ala
                325                 330                 335

Glu Asn Glu Leu Ala Asp Thr Met Gln Ile Val Ser Leu Gln Leu Asn
            340                 345                 350

Lys Met Lys Ser Arg Lys Ser Cys Gly Ile Ala Val Gly Thr Thr Val
        355                 360                 365

Val Asp Ala Asp Lys Tyr Ala Val Thr Ile Glu Thr Arg Leu Ile Asp
370                 375                 380

Glu Arg Ala Ala His Val Asn Ala Gln Phe Arg Phe
385                 390                 395

<210> SEQ ID NO 9
<211> LENGTH: 397
<212> TYPE: PRT
<213> ORGANISM: Chlamydia trachomatis

<400> SEQUENCE: 9

Met Lys Lys Leu Leu Lys Ser Val Leu Val Phe Ala Ala Leu Ser Ser
  1               5                  10                  15

Ala Ser Ser Leu Gln Ala Leu Pro Val Gly Asn Pro Ala Glu Pro Ser
                 20                  25                  30

Leu Met Ile Asp Gly Ile Leu Trp Glu Gly Phe Gly Gly Asp Pro Cys
             35                  40                  45

Asp Pro Cys Thr Thr Trp Cys Asp Ala Ile Ser Met Arg Val Gly Tyr
         50                  55                  60

Tyr Gly Asp Phe Val Phe Asp Arg Val Leu Lys Thr Asp Val Asn Lys
 65                  70                  75                  80

Glu Phe Gln Met Gly Ala Ala Pro Thr Thr Ser Asp Val Ala Gly Leu
                 85                  90                  95

Gln Asn Asp Pro Thr Thr Asn Asn Ala Arg Pro Asn Pro Ala Tyr Gly
                100                 105                 110

Lys His Met Gln Asp Ala Glu Met Phe Thr Asn Ala Ala Tyr Met Ala
            115                 120                 125

Leu Asn Ile Trp Asp Arg Phe Asp Val Phe Cys Thr Leu Gly Ala Thr
130                 135                 140

Thr Gly Tyr Leu Lys Gly Asn Ser Ala Ser Phe Asn Leu Val Gly Leu
145                 150                 155                 160

Phe Gly Thr Lys Thr Gln Ser Ser Ser Phe Asn Thr Ala Lys Leu Ile
                165                 170                 175

Pro Thr Ala Ser Leu Asn Glu Ala Val Val Glu Leu Tyr Ile Asn Thr
            180                 185                 190
```

```
Thr Phe Ala Trp Ser Val Gly Ala Arg Ala Ala Leu Trp Glu Cys Gly
        195                 200                 205

Cys Ala Thr Leu Gly Ala Ser Phe Gln Tyr Ala Gln Ser Lys Pro Lys
    210                 215                 220

Val Glu Glu Leu Asn Val Leu Cys Asn Ala Ser Glu Phe Thr Ile Asn
225                 230                 235                 240

Lys Pro Lys Gly Tyr Val Gly Ala Glu Phe Pro Leu Asn Ile Thr Ala
                245                 250                 255

Gly Thr Glu Ala Ala Thr Gly Thr Lys Asp Ala Ser Ile Asp Tyr Asn
                260                 265                 270

Glu Trp Gln Ala Ser Leu Ala Leu Ser Tyr Arg Leu Asn Met Phe Thr
            275                 280                 285

Pro Tyr Ile Gly Val Lys Trp Ser Arg Val Ser Phe Asp Ala Asp Thr
        290                 295                 300

Ile Arg Ile Ala Gln Pro Lys Leu Ala Glu Ala Ile Leu Asp Val Thr
305                 310                 315                 320

Thr Leu Asn Pro Thr Ile Ala Gly Lys Gly Ser Val Val Ser Ala Gly
                325                 330                 335

Thr Asp Asn Glu Leu Ala Asp Thr Met Gln Ile Val Ser Leu Gln Leu
                340                 345                 350

Asn Lys Met Lys Ser Arg Lys Ser Cys Gly Ile Ala Val Gly Thr Thr
            355                 360                 365

Ile Val Asp Ala Asp Lys Tyr Ala Val Thr Val Glu Ala Arg Leu Ile
370                 375                 380

Asp Glu Arg Ala Ala His Val Asn Ala Gln Phe Arg Phe
385                 390                 395

<210> SEQ ID NO 10
<211> LENGTH: 397
<212> TYPE: PRT
<213> ORGANISM: Chlamydia trachomatis

<400> SEQUENCE: 10

Met Lys Lys Leu Leu Lys Ser Val Leu Val Phe Ala Ala Leu Ser Ser
  1               5                  10                  15

Ala Ser Ser Leu Gln Ala Leu Pro Val Gly Asn Pro Ala Glu Pro Ser
                 20                  25                  30

Leu Met Ile Asp Gly Ile Leu Trp Glu Gly Phe Gly Gly Asp Pro Cys
             35                  40                  45

Asp Pro Cys Ala Thr Trp Cys Asp Ala Ile Ser Met Arg Val Gly Tyr
     50                  55                  60

Tyr Gly Asp Phe Val Phe Asp Arg Val Leu Lys Thr Asp Val Asn Lys
 65                  70                  75                  80

Glu Phe Gln Met Gly Ala Ala Pro Thr Thr Asn Asp Ala Ala Asp Leu
                 85                  90                  95

Gln Asn Asp Pro Lys Thr Asn Val Ala Arg Pro Asn Pro Ala Tyr Gly
                100                 105                 110

Lys His Met Gln Asp Ala Glu Met Phe Thr Asn Ala Ala Tyr Met Ala
            115                 120                 125

Leu Asn Ile Trp Asp Arg Phe Asp Val Phe Cys Thr Leu Gly Ala Thr
130                 135                 140

Thr Gly Tyr Leu Lys Gly Asn Ser Ala Ser Phe Asn Leu Val Gly Leu
145                 150                 155                 160

Phe Gly Thr Lys Thr Lys Ser Ser Asp Phe Asn Thr Ala Lys Leu Val
```

```
                165                 170                 175
Pro Asn Ile Ala Leu Asn Arg Ala Val Val Glu Leu Tyr Thr Asp Thr
            180                 185                 190

Thr Phe Ala Trp Ser Val Gly Ala Arg Ala Ala Leu Trp Glu Cys Gly
        195                 200                 205

Cys Ala Thr Leu Gly Ala Ser Phe Gln Tyr Ala Gln Ser Lys Pro Lys
        210                 215                 220

Val Glu Glu Leu Asn Val Leu Cys Asn Ala Ser Glu Phe Thr Ile Asn
225                 230                 235                 240

Lys Pro Lys Gly Tyr Val Gly Ala Glu Phe Pro Leu Asp Ile Thr Ala
                245                 250                 255

Gly Thr Glu Ala Ala Thr Gly Thr Lys Asp Ala Ser Ile Asp Tyr Asn
            260                 265                 270

Glu Trp Gln Ala Ser Leu Ala Leu Ser Tyr Arg Leu Asn Met Phe Thr
        275                 280                 285

Pro Tyr Ile Gly Val Lys Trp Ser Arg Val Ser Phe Asp Ala Asp Thr
        290                 295                 300

Ile Arg Ile Ala Gln Pro Lys Leu Ala Glu Ala Ile Leu Asp Val Thr
305                 310                 315                 320

Thr Leu Asn Pro Thr Ile Ala Gly Lys Gly Thr Val Val Ala Ser Gly
                325                 330                 335

Ser Asp Asn Asp Leu Ala Asp Thr Met Gln Ile Val Ser Leu Gln Leu
            340                 345                 350

Asn Lys Met Lys Ser Arg Lys Ser Cys Gly Ile Ala Val Gly Thr Thr
        355                 360                 365

Ile Val Asp Ala Asp Lys Tyr Ala Val Thr Val Glu Thr Arg Leu Ile
        370                 375                 380

Asp Glu Arg Ala Ala His Val Asn Ala Gln Phe Arg Phe
385                 390                 395

<210> SEQ ID NO 11
<211> LENGTH: 387
<212> TYPE: PRT
<213> ORGANISM: Chlamydia trachomatis

<400> SEQUENCE: 11

Met Lys Lys Leu Leu Lys Ser Val Leu Ala Phe Ala Val Leu Gly Ser
  1               5                  10                  15

Ala Ser Ser Leu His Ala Leu Pro Val Gly Asn Pro Ala Glu Pro Ser
            20                  25                  30

Leu Met Ile Asp Gly Ile Leu Trp Glu Gly Phe Gly Gly Asp Pro Cys
        35                  40                  45

Asp Pro Cys Thr Thr Trp Cys Asp Ala Ile Ser Leu Arg Leu Gly Tyr
    50                  55                  60

Tyr Gly Asp Phe Val Phe Asp Arg Val Leu Lys Thr Asp Val Asn Lys
65                  70                  75                  80

Gln Phe Glu Met Gly Ala Ala Pro Thr Gly Asp Ala Asp Leu Thr Thr
                85                  90                  95

Ala Pro Thr Pro Ala Ser Arg Glu Asn Pro Ala Tyr Gly Lys His Met
            100                 105                 110

Gln Asp Ala Glu Met Phe Thr Asn Ala Ala Tyr Met Ala Leu Asn Ile
        115                 120                 125

Trp Asp Arg Phe Asp Val Phe Cys Thr Leu Gly Ala Thr Ser Gly Tyr
    130                 135                 140
```

```
Leu Lys Gly Asn Ser Ala Ala Phe Asn Leu Val Gly Leu Phe Gly Arg
145                 150                 155                 160

Asp Glu Thr Ala Val Ala Ala Asp Asp Ile Pro Asn Val Ser Leu Ser
            165                 170                 175

Gln Ala Val Val Glu Leu Tyr Thr Asp Thr Ala Phe Ala Trp Ser Val
        180                 185                 190

Gly Ala Arg Ala Ala Leu Trp Glu Cys Gly Cys Ala Thr Leu Gly Ala
        195                 200                 205

Ser Phe Gln Tyr Ala Gln Ser Lys Pro Lys Val Glu Glu Leu Asn Val
    210                 215                 220

Leu Cys Asn Ala Ala Glu Phe Thr Ile Asn Lys Pro Lys Gly Tyr Val
225                 230                 235                 240

Gly Gln Glu Phe Pro Leu Asn Ile Lys Ala Gly Thr Val Ser Ala Thr
                245                 250                 255

Asp Thr Lys Asp Ala Ser Ile Asp Tyr Asn Glu Trp Gln Ala Ser Leu
            260                 265                 270

Ala Leu Ser Tyr Arg Leu Asn Met Phe Thr Pro Tyr Ile Gly Val Lys
        275                 280                 285

Trp Ser Arg Ala Ser Phe Asp Ala Asp Thr Ile Arg Ile Ala Gln Pro
        290                 295                 300

Lys Leu Glu Thr Ser Ile Leu Lys Met Thr Thr Trp Asn Pro Thr Ile
305                 310                 315                 320

Ser Gly Ser Gly Ile Asp Val Asp Thr Lys Ile Thr Asp Thr Leu Gln
                325                 330                 335

Ile Val Ser Leu Gln Leu Asn Lys Met Lys Ser Arg Lys Ser Cys Gly
            340                 345                 350

Leu Ala Ile Gly Thr Thr Ile Val Asp Ala Asp Lys Tyr Ala Val Thr
        355                 360                 365

Val Glu Thr Arg Leu Ile Asp Glu Arg Ala Ala His Val Asn Ala Gln
370                 375                 380

Phe Arg Phe
385

<210> SEQ ID NO 12
<211> LENGTH: 404
<212> TYPE: PRT
<213> ORGANISM: Chlamydia trachomatis

<400> SEQUENCE: 12

Met Lys Lys Leu Leu Lys Ser Val Leu Ala Phe Ala Val Leu Gly Ser
1               5                   10                  15

Ala Ser Ser Leu His Ala Leu Pro Val Gly Asn Pro Ala Glu Pro Ser
            20                  25                  30

Leu Met Ile Asp Gly Ile Leu Trp Glu Gly Phe Gly Gly Asp Pro Cys
        35                  40                  45

Asp Pro Cys Thr Thr Trp Cys Asp Ala Ile Ser Leu Arg Leu Gly Tyr
    50                  55                  60

Tyr Gly Asp Phe Val Phe Asp Arg Val Leu Lys Thr Asp Val Asn Lys
65                  70                  75                  80

Gln Phe Glu Met Gly Pro Val Pro Thr Thr Asp Thr Asp Ala Ala
                85                  90                  95

Ala Asp Ile Thr Thr Ser Thr Pro Arg Glu Asn Pro Ala Tyr Gly Lys
            100                 105                 110

His Met Gln Asp Ala Glu Met Phe Thr Asn Ala Ala Tyr Met Ala Leu
        115                 120                 125
```

```
Asn Ile Trp Asp Arg Phe Asp Val Phe Cys Thr Leu Gly Ala Thr Ser
            130                 135                 140

Gly Tyr Leu Lys Gly Asn Ser Ala Ser Phe Asn Leu Val Gly Leu Phe
145                 150                 155                 160

Gly Asp Gly Val Ala Asn Ala Asn Ala Ile Ala Thr Val Ala Ala
                165                 170                 175

Asp Ser Leu Pro Asn Val Ser Leu Ser Gln Ala Val Val Glu Leu Tyr
                180                 185                 190

Thr Asp Thr Ala Phe Ala Trp Ser Val Gly Ala Arg Ala Ala Leu Trp
            195                 200                 205

Glu Cys Gly Cys Ala Thr Leu Gly Ala Ser Phe Gln Tyr Ala Gln Ser
    210                 215                 220

Lys Pro Lys Val Glu Glu Leu Asn Val Leu Cys Asn Ala Ala Gln Phe
225                 230                 235                 240

Thr Ile Asn Lys Pro Lys Gly Tyr Val Gly Lys Glu Phe Pro Leu Ala
                245                 250                 255

Leu Thr Ala Gly Thr Asp Ser Ala Thr Asp Thr Lys Asp Ala Ser Ile
                260                 265                 270

Asp Tyr Asn Glu Trp Gln Ala Ser Leu Ala Leu Ser Tyr Arg Leu Asn
            275                 280                 285

Met Phe Thr Pro Tyr Ile Gly Val Lys Trp Ser Arg Ala Ser Phe Asp
    290                 295                 300

Ala Asp Thr Ile Arg Ile Ala Gln Pro Lys Leu Ala Glu Ala Ile Leu
305                 310                 315                 320

Asp Val Thr Thr Trp Asn Pro Thr Ile Ala Gly Ala Gly Thr Ile Ala
                325                 330                 335

Asp Gly Thr Gly Ala Ala Thr Ala Asn Gly Leu Ala Asp Thr Leu
                340                 345                 350

Gln Ile Val Ser Leu Gln Leu Asn Lys Met Lys Ser Arg Lys Ser Cys
        355                 360                 365

Gly Leu Ala Ile Gly Thr Thr Ile Val Asp Ala Asp Lys Tyr Ala Val
    370                 375                 380

Thr Val Glu Thr Arg Leu Ile Asp Glu Arg Ala Ala His Val Asn Ala
385                 390                 395                 400

Gln Phe Arg Phe

<210> SEQ ID NO 13
<211> LENGTH: 389
<212> TYPE: PRT
<213> ORGANISM: Chlamydia trachomatis

<400> SEQUENCE: 13

Met Lys Lys Leu Leu Lys Ser Ala Leu Leu Phe Ala Thr Thr Gly Ser
  1               5                  10                  15

Ala Leu Ser Leu Gln Ala Leu Pro Val Gly Asn Pro Ala Glu Pro Ser
                 20                  25                  30

Leu Leu Ile Asp Gly Thr Met Trp Glu Gly Ala Ser Gly Asp Pro Cys
             35                  40                  45

Asp Pro Cys Ser Thr Trp Cys Asp Ala Ile Ser Ile Arg Ala Gly Tyr
         50                  55                  60

Tyr Gly Asp Tyr Val Phe Asp Arg Ile Leu Lys Val Asp Val Asn Lys
 65                  70                  75                  80

Thr Ile Ser Met Gly Thr Ala Pro Thr Gly Asn Ala Ala Ala Asp Phe
                 85                  90                  95
```

```
Lys Thr Val Ala Asp Arg Asn Asn Ile Ala Tyr Gly Lys His Met Gln
                100                 105                 110

Asp Ala Glu Trp Ser Thr Asn Ala Ala Phe Leu Ala Leu Asn Ile Trp
            115                 120                 125

Asp Arg Phe Asp Val Phe Cys Thr Leu Gly Ala Ser Asn Gly Tyr Leu
        130                 135                 140

Lys Ala Asn Ala Ala Ala Phe Asn Leu Val Gly Leu Leu Gly Val Thr
145                 150                 155                 160

Gly Thr Asp Leu Gln Gly Gln Tyr Pro Asn Val Ala Ile Ser Gln Gly
                165                 170                 175

Leu Val Glu Leu Tyr Thr Asp Thr Thr Phe Ser Trp Ser Val Gly Ala
            180                 185                 190

Arg Gly Ala Leu Trp Glu Cys Gly Cys Ala Thr Leu Gly Ala Glu Phe
        195                 200                 205

Gln Tyr Ala Gln Ser Asn Pro Lys Ile Glu Met Leu Asn Val Ile Ser
    210                 215                 220

Ser Pro Thr Gln Phe Val Ile His Lys Pro Arg Gly Tyr Lys Gly Thr
225                 230                 235                 240

Ala Ala Asn Phe Pro Leu Pro Leu Thr Ala Gly Thr Glu Ser Ala Thr
                245                 250                 255

Asp Thr Lys Ser Ala Thr Ile Lys Tyr Asn Glu Trp Gln Ile Gly Leu
            260                 265                 270

Ala Leu Ser Tyr Arg Leu Asn Met Leu Val Pro Tyr Ile Gly Val Asn
        275                 280                 285

Trp Ser Arg Ala Thr Phe Asp Ala Asp Ser Ile Arg Ile Ala Gln Pro
    290                 295                 300

Lys Leu Pro Thr Ala Ile Leu Asn Leu Thr Thr Trp Asn Pro Thr Leu
305                 310                 315                 320

Leu Gly Glu Ala Thr Thr Ile Asn Thr Gly Ala Lys Tyr Ala Asp Gln
                325                 330                 335

Leu Gln Ile Ala Ser Leu Gln Ile Asn Lys Met Lys Ser Arg Lys Ala
            340                 345                 350

Cys Gly Ile Ala Val Gly Ala Thr Leu Ile Asp Ala Asp Lys Trp Ser
        355                 360                 365

Ile Thr Gly Glu Ala Arg Leu Ile Asn Glu Arg Ala Ala His Val Asn
    370                 375                 380

Ala Gln Phe Arg Phe
385

<210> SEQ ID NO 14
<211> LENGTH: 402
<212> TYPE: PRT
<213> ORGANISM: Chlamydia trachomatis

<400> SEQUENCE: 14

Met Lys Lys Leu Leu Lys Ser Ala Leu Leu Phe Ala Ala Thr Gly Ser
1               5                   10                  15

Ala Leu Ser Leu Gln Ala Leu Pro Val Gly Asn Pro Ala Glu Pro Ser
            20                  25                  30

Leu Leu Ile Asp Gly Thr Met Trp Glu Gly Ala Ser Gly Asp Pro Cys
        35                  40                  45

Asp Pro Cys Ala Thr Trp Cys Asp Ala Ile Ser Ile Arg Ala Gly Tyr
    50                  55                  60

Tyr Gly Asp Tyr Val Phe Asp Arg Val Leu Lys Val Asp Val Asn Lys
```

-continued

```
                65                  70                  75                  80
Thr Phe Ser Gly Met Ala Ala Thr Pro Thr Gln Ala Thr Gly Asn Ala
                    85                  90                  95
Ser Asn Thr Asn Gln Pro Glu Ala Asn Gly Arg Pro Asn Ile Ala Tyr
                100                 105                 110
Gly Arg His Met Glu Asp Ala Glu Trp Phe Ser Asn Ala Ala Phe Leu
                115                 120                 125
Ala Leu Asn Ile Trp Asp Arg Phe Asp Ile Phe Cys Thr Leu Gly Ala
            130                 135                 140
Ser Asn Gly Tyr Phe Lys Ala Ser Ala Ala Phe Asn Leu Val Gly
145                 150                 155                 160
Leu Ile Gly Phe Ser Ala Ala Ser Ser Ile Ser Thr Asp Leu Pro Thr
                165                 170                 175
Gln Leu Pro Asn Val Gly Ile Thr Gln Gly Val Val Glu Phe Tyr Thr
                180                 185                 190
Asp Thr Ser Phe Ser Trp Ser Val Gly Ala Arg Gly Ala Leu Trp Glu
            195                 200                 205
Cys Gly Cys Ala Thr Leu Gly Ala Glu Phe Gln Tyr Ala Gln Ser Asn
        210                 215                 220
Pro Lys Ile Glu Met Leu Asn Val Thr Ser Ser Pro Ala Gln Phe Val
225                 230                 235                 240
Ile His Lys Pro Arg Gly Tyr Lys Gly Ala Ser Ser Asn Phe Pro Leu
                245                 250                 255
Pro Ile Thr Ala Gly Thr Thr Glu Ala Thr Asp Thr Lys Ser Ala Thr
                260                 265                 270
Ile Lys Tyr Asn Glu Trp Gln Val Gly Leu Ala Leu Ser Tyr Arg Leu
            275                 280                 285
Asn Met Leu Val Pro Tyr Ile Gly Val Asn Trp Ser Arg Ala Thr Phe
        290                 295                 300
Asp Ala Asp Thr Ile Arg Ile Ala Gln Pro Lys Leu Lys Ser Glu Ile
305                 310                 315                 320
Leu Asn Ile Thr Thr Trp Asn Pro Ser Leu Ile Gly Ser Thr Thr Ala
                325                 330                 335
Leu Pro Asn Asn Ser Gly Lys Asp Val Leu Ser Asp Val Leu Gln Ile
                340                 345                 350
Ala Ser Ile Gln Ile Asn Lys Met Lys Ser Arg Lys Ala Cys Gly Val
            355                 360                 365
Ala Val Gly Ala Thr Leu Ile Asp Ala Asp Lys Trp Ser Ile Thr Gly
        370                 375                 380
Glu Ala Arg Leu Ile Asn Glu Arg Ala Ala His Met Asn Ala Gln Phe
385                 390                 395                 400
Arg Phe

<210> SEQ ID NO 15
<211> LENGTH: 389
<212> TYPE: PRT
<213> ORGANISM: Chlamydia trachomatis

<400> SEQUENCE: 15

Met Lys Lys Leu Leu Lys Ser Ala Leu Leu Ser Ala Ala Phe Ala Gly
 1               5                  10                  15
Ser Val Gly Ser Leu Gln Ala Leu Pro Val Gly Asn Pro Ser Asp Pro
                20                  25                  30
Ser Leu Leu Ile Asp Gly Thr Ile Trp Glu Gly Ala Ala Gly Asp Pro
```

-continued

```
                35                  40                  45
Cys Asp Pro Cys Ala Thr Trp Cys Asp Ala Ile Ser Leu Arg Ala Gly
 50                  55                  60

Phe Tyr Gly Asp Tyr Val Phe Asp Arg Ile Leu Lys Val Asp Ala Pro
 65                  70                  75                  80

Lys Thr Phe Ser Met Gly Ala Lys Pro Thr Gly Ser Ala Ala Ala Asn
                 85                  90                  95

Tyr Thr Thr Ala Val Asp Arg Pro Asn Pro Ala Tyr Asn Lys His Leu
                100                 105                 110

His Asp Ala Glu Trp Phe Thr Asn Ala Gly Phe Ile Ala Leu Asn Ile
                115                 120                 125

Trp Asp Arg Phe Asp Val Phe Cys Thr Leu Gly Ala Ser Asn Gly Tyr
130                 135                 140

Ile Arg Gly Asn Ser Thr Ala Phe Asn Leu Val Gly Leu Phe Gly Val
145                 150                 155                 160

Lys Gly Thr Thr Val Asn Ala Asn Glu Leu Pro Asn Val Ser Leu Ser
                165                 170                 175

Asn Gly Val Val Glu Leu Tyr Thr Asp Thr Ser Phe Ser Trp Ser Val
                180                 185                 190

Gly Ala Arg Gly Ala Leu Trp Glu Cys Gly Cys Ala Thr Leu Gly Ala
                195                 200                 205

Glu Phe Gln Tyr Ala Gln Ser Lys Pro Lys Val Glu Glu Leu Asn Val
210                 215                 220

Ile Cys Asn Val Ser Gln Phe Ser Val Asn Lys Pro Lys Gly Tyr Lys
225                 230                 235                 240

Gly Val Ala Phe Pro Leu Pro Thr Asp Ala Gly Val Ala Thr Ala Thr
                245                 250                 255

Gly Thr Lys Ser Ala Thr Ile Asn Tyr Asn Glu Trp Gln Val Gly Ala
                260                 265                 270

Ser Leu Ser Tyr Arg Leu Asn Ser Leu Val Pro Tyr Ile Gly Val Gln
                275                 280                 285

Trp Ser Arg Ala Thr Phe Asp Ala Asp Asn Ile Arg Ile Ala Gln Pro
290                 295                 300

Lys Leu Pro Thr Ala Val Leu Asn Leu Thr Ala Trp Asn Pro Ser Leu
305                 310                 315                 320

Leu Gly Asn Ala Thr Ala Leu Ser Thr Thr Asp Ser Phe Ser Asp Phe
                325                 330                 335

Met Gln Ile Val Ser Cys Gln Ile Asn Lys Phe Lys Ser Arg Lys Ala
                340                 345                 350

Cys Gly Val Thr Val Gly Ala Thr Leu Val Asp Ala Asp Lys Trp Ser
                355                 360                 365

Leu Thr Ala Glu Ala Arg Leu Ile Asn Glu Arg Ala Ala His Val Ser
370                 375                 380

Gly Gln Phe Arg Phe
385
```

<210> SEQ ID NO 16
<211> LENGTH: 35
<212> TYPE: DNA
<213> ORGANISM: Chlamydia trachomatis

<400> SEQUENCE: 16
ggggatccgc caccatgctg cctgtgggga atcct                         35

```
<210> SEQ ID NO 17
<211> LENGTH: 28
<212> TYPE: DNA
<213> ORGANISM: Chlamydia trachomatis

<400> SEQUENCE: 17
ggggctcgag ctattaacgg aactgagc                                          28
```